(12) United States Patent
Flavell et al.

(10) Patent No.: US 10,774,392 B2
(45) Date of Patent: *Sep. 15, 2020

(54) COMPOSITIONS AND METHODS FOR IDENTIFYING SECRETORY ANTIBODY-BOUND MICROBES

(71) Applicant: Yale University, New Haven, CT (US)

(72) Inventors: Richard Flavell, Guilford, CT (US); Noah Palm, New Haven, CT (US); Marcel de Zoete, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/540,408

(22) Filed: Aug. 14, 2019

(65) Prior Publication Data

US 2020/0002751 A1 Jan. 2, 2020

Related U.S. Application Data

(63) Continuation of application No. 15/664,150, filed on Jul. 31, 2017, now Pat. No. 10,428,392, which is a continuation of application No. 14/775,328, filed as application No. PCT/US2014/023967 on Mar. 12, 2014, now Pat. No. 9,758,838.

(60) Provisional application No. 61/777,519, filed on Mar. 12, 2013.

(51) Int. Cl.
| | | |
|---|---|---|
| A01N 63/00 | (2020.01) | |
| C12Q 1/689 | (2018.01) | |
| C12Q 1/6806 | (2018.01) | |
| A61K 35/741 | (2015.01) | |
| A61K 39/02 | (2006.01) | |
| A61K 35/00 | (2006.01) | |

(52) U.S. Cl.
CPC ............ *C12Q 1/689* (2013.01); *A61K 35/741* (2013.01); *A61K 39/0208* (2013.01); *C12Q 1/6806* (2013.01); *A61K 2035/115* (2013.01)

(58) Field of Classification Search
CPC .................................................... C12Q 1/689
See application file for complete search history.

(56) References Cited

U.S. PATENT DOCUMENTS

| | | | |
|---|---|---|---|
| 5,599,795 A | 2/1997 | McCann | |
| 6,290,960 B1 | 9/2001 | Kink | |
| 8,211,432 B2 | 7/2012 | Hoeoek | |
| 9,758,838 B2 | 9/2017 | Flavell | |
| 10,428,392 B2 * | 10/2019 | Flavell | C12Q 1/6806 |
| 2005/0100531 A1 | 5/2005 | Bienenstock | |
| 2006/0073161 A1 | 4/2006 | Breton | |
| 2007/0231336 A1 | 10/2007 | Thomas | |
| 2012/0027799 A1 | 2/2012 | Sears | |
| 2012/0238468 A1 | 9/2012 | Tuk | |
| 2012/0276132 A1 | 11/2012 | Feng | |
| 2016/0017409 A1 | 1/2016 | Flavell | |
| 2018/0030517 A1 | 2/2018 | Flavell | |
| 2019/0083599 A1 | 3/2019 | Flavell | |

FOREIGN PATENT DOCUMENTS

| | | |
|---|---|---|
| JP | H05132428 A | 5/1993 |
| KR | 20120082529 A | 7/2012 |
| WO | 2010005836 A2 | 1/2010 |
| WO | 2010115092 | 10/2010 |
| WO | 2011005756 A1 | 1/2011 |
| WO | 2012103337 A2 | 8/2012 |
| WO | 2013012332 A1 | 1/2013 |
| WO | 2013036290 A1 | 3/2013 |
| WO | 2013166031 A1 | 11/2013 |
| WO | 2016033439 | 3/2016 |

OTHER PUBLICATIONS

Abraham and Cho, "Inflammatory Bowel Disease," 2009, New Engl. J. Med. 361:2066-2078, downloaded from nejm.org on Jan. 25, 2019.

Atarashi et al., 2011, Induction of Colonic Regulatory T Cells by Indigenous Clostridium Species. Science 331:337.

Barreto et al., "Causes of variation in BCG vaccine efficacy: Examining evidence from the BCG REVAC cluster randomized trial to explore the masking and the blocking hypotheses", VACCINE 32(30):3759-3764 (2014).

Basset, C. et al., "Are Helicobacter species and enterotoxigenic *Bacteroides fragilis* involved in inflammatory bowel disease?" Dig. Dis. Sci., vol. 49, No. 9, pp. 1425-32 (2004).

Belkaid and Hand, 2014, "Role of the microbiota in immunity and inflammation," Cell 157(1):121-141.

Bemark et al., 2012, "Induction of gut IgA production through T cell-dependent and T cell-independent pathways," Ann NY Acad Sci 1247:97-116.

Ben-Amor et al., 2005, "Genetic diversity of viable, injured, and dead fecal bacteria assessed by fluorescence-activated cell sorting and 16S rRNA gene analysis.," Appl Environ Microb 71(8):4679-4689, downloaded from http://aem.asm.org on Jan. 25, 2019.

Blumberg and Powrie, (2012), Microbiota, Disease, and Back to Health: A Metastable Journey. Science translational medicine 4:137rv7. (9 pages).

Brandtzaeg, "Secretory IgA: Designed for Anti-Microbial Defense," Frontiers in Immunology, vol. 4, Jan. 1, 2013 (Jan. 1, 2013), Article 222, 17 pages.

Chow et al., 2011, Pathobionts of the Gastrointestinal Microbiota and Inflammatory Disease. Current opinion in immunology 23:473. (14 pages).

(Continued)

*Primary Examiner* — Albert M Navarro

(74) *Attorney, Agent, or Firm* — Riverside Law LLP

(57) ABSTRACT

The invention relates to the identification of secretory antibody-bound bacteria in the microbiota in a subject that influence the development and progression of inflammatory diseases and disorders. Thus, the invention relates to compositions and methods for detecting and identifying the constituents of a subject's microbiota, methods of modifying the constituents of the microbiota, and methods for treating inflammatory diseases and disorders in a subject in need thereof.

22 Claims, 21 Drawing Sheets

(56) References Cited

OTHER PUBLICATIONS

Cong et al., 2009, "A dominant, coordinated T regulatory cell-IgA response to the intestinal microbiota," P Natl Acad Sci USA 106(46):19256-19261.
Cullender et al., 2013, "Innate and adaptive immunity interact to quench microbiome flagellar motility in the gut," Cell Host Microbe 14(5):571-581.
D'Auria et al., 2013, "Active and secreted IgA-coated bacterial fractions from the human gut reveal an under-represented microbiota core," Sci Rep 3:3515, 9 pages.
Dantas et al., 2013, "Experimental Approaches for Defining Functional Roles of Microbes in the Human Gut," Annu Rev Microbial 67:459-475.
Database WPI: Week 199326, Thomson Scientific. London. GB; Accession No. AN 1993-208829, and JPH05132428A, Lion Corp., Abstract (May 28, 1993). (1 page).
DePalma et al., 'Intestinal dysbiosis and reduced immunoglobulin-coated bacteria associated with coeliac disease in children', BMC Microbiology, Biomed. Central Ltd. GB, vol. 10, No. 1, pp. 1-7 (Feb. 24, 2010).
Eckmann et al., "Opposing functions of IKKß during acute and chronic intestinal inflammation", Proc Natl Acad Sci, vol. 105, No. 39, pp. 15058-15063 (2008).
Elinav et al., 2011, "NLRP6 Inflammasome Regulates Colonic Microbial Ecology and risk for Colitis." Cell, 145(5):745-757.
Etebu et al., Antibiotics: Classification and mechanisms of action with emphasis on molecular perspectives. (International Journal of Applied Microbiology and Biotechnology Research vol. 4, pp. 90-101) (Year: 2016).
Everard et al., 2013, Cross-talk between Akkermansia muciniphila and intestinal epithelium controls diet-induced obesity. Proceedings of the National Academy of Sciences of the United States of America 110:9066, 6 pages.
Extended European Search Report issued by the European Patent Office for Application No. 14774155.7, dated Aug. 3, 2016, 10 pages.
Extended European Search Report issued by the European Patent Office for Application No. 15835666.7, dated Feb. 27, 2018, 13 pages.
Extended European Search Report issued by the European Patent Office for Application No. 18197005.4, dated Dec. 12, 2018, 12 pages.
Final Office Action issued by the United States Patent and Trademark Office for U.S. Appl. No. 15/664,150, dated Feb. 11, 2019, 7 pages.
Fujihashi et al., 1996, "gamma/delta T cell-deficient mice have impaired mucosal immunoglobulin A responses," J Exp Med 183(4):1929-1935, Downloaded from jem.rupress.org on Jan. 25, 2019.
Gevers et al., 2014, "The treatment-naive microbiome in new-onset Crohn's disease," Cell Host Microbe 15(3):382-392.
Hapfelmeier et al., 2010, Reversible microbial colonization of germ-free mice reveals the dynamics of IgA immune responses. Science 328:1705, 10 pages.
Hirota et al., 2013, "TH17 cell plasticity in Peyer's patches is responsible for; induction of T cell-dependent IgA responses," Nat Immunol 14(4):372-379.
Hooper et al., 2012, Interactions between the microbiota and the immune system. Science 336:1268, 16 pages.
Huttenhower and Consortium, 2012, "Structure, function and diversity of the healthy human microbiome," Nature 486:207-214.
International Search Report and Written Opinion issued by the International Searching Authority for Application No. PCT/US2014/023967, dated Jun. 9, 2014, 10 pages.
International Search Report and Written Opinion issued by the International Searching Authority for Application No. PCT/US2015/047400, dated Feb. 19, 2016, 11 pages.
Ivanov et al., 2009, Induction of intestinal Th17 Cells by Segmented Filamentous Bacteria. Cell 139:485, 14 pages.

Jeon et al., 2012, Probiotic Bifidobacterium breve Induces IL-10-Producing Trl Cells in the Colon. PLoS pathogens 8:e1002714. (15 pages).
Kato et al., 2014, "Gut TFH and IgA: key players for regulation of bacterial communities and immune homeostasis," Immunol Cell Biol 92:49-56.
Kawamoto et al., 2012, "The inhibitory receptor PD-1 regulates IgA selection and bacterial composition in the gut," Science 336:485-489.
Knights et al., 2013, "Advances in inflammatory bowel disease pathogenesis: linking host genetics and the microbiome," Gut 62:1505-1510.
Kriegel et al., 2011, Naturally transmitted segmented filamentous bacteria segregate with diabetes protection in nonobese diabetic mice Proceedings of the National Academy of Sciences of the United States of America 108:115488, 6 pages.
Kullberg et al., 1998, "Helicobacter hepaticus triggers colitis in specific-pathogen-free interleukin-10 (IL-10)-deficient mice through an IL-12- and gamma interferon-dependent mechanism," Infect Immun 66(11):5157-5166.
L A Van Der Waaij et al., 'In vivo IgA coating of anaerobic bacteria in human faeces', Gut, vol. 38, pp. 348-354 (1996).
Littman and Pamer, 2011, Role of the Commensal Microbiota in Normal and Pathogenic Host Immune Responses. Cell host & microbe 10:311. (13 pages).
Lozupone et al., 2012, Diversity, stability and resilience of the human gut microbiota. Nature 489:220. (26 pages).
Macpherson 2012, The habitat, double life, citizenship, and forgetfulness of IgA, Immunological reviews 245:132. (15 pages).
Macpherson and Uhr, 2004, Induction of Protective IgA by Intestinal Dendritic Cells Carrying Commensal Bacteria, Science 303:1662. (4 pages).
Macpherson et al., 2000, A Primitive T Cell-Independent Mechanism of Intestinal Mucosal IgA Responses to Commensal Bacteria, Science 288:2222, 1 page.
Mathias and Corthesy, 2011, "N-Glycans on secretory component: mediators of the interaction between secretory IgA and gram-positive commensals sustaining intestinal homeostasis," Gut Microbes 2(5):287-293.
Maurice et al., 2013, "Xenobiotics shape the physiology and gene expression of the active human gut microbiome," Cell 152(1-2):39-50.
Mazmanian et al., 2008, A microbial symbiosis factor prevents intestinal inflammatory disease. Nature 453:620. (6 pages).
Nadal et al., 'Shifts in clostridia, bacteroides and immunoglobulin-coating fecal bacteria associated with weight loss in obese adolescents', International Journal of Obesity, vol. 33, No. 7, pp. 758-767 (Jul. 1, 2009).
Nagaro et al., Nontoxigenic Clostridium difficile Protects Hamsters against Challenge with Historic and Epidemic Strains of Toxigenic BI/NAP1/027 C. difficile Antimicrob Agents Chemother 57:5266-5270 (2013).
Nasser et al., "Long-Lasting Protective Antiviral Immunity Induced by Passive Immunotherapies Requires both Neutralizing and Effector Functions of the Administered Monoclonal Antibody" Journal of Virology, Oct. 2010, vol. 84 (19), p. 10169-10181.
Non-Final Office Action issued by the United States Patent and Trademark Office for U.S. Appl. No. 14/775,328, dated Dec. 7, 2016, 7 pages.
Non-Final Office Action issued by the United States Patent and Trademark Office for U.S. Appl. No. 15/664,150, dated Oct. 22, 2018, 9 pages.
Notice of Allowance dated May 21, 2019 for U.S. Appl. No. 15/664,150 (pp. 1-5).
Office Action dated Feb. 11, 2019 for U.S. Appl. No. 15/664,150 (pp. 1-7).
Office Action dated Oct. 22, 2018 for U.S. App. No. 15/664,150 (pp. 1-8).
Pabst, 2012, New concepts in the generation and functions of IgA. Nature Reviews Immunology; 12:821. (12 pages).
Packey and Sartor, 2009, "Commensal bacteria, traditional and opportunistic pathogens, dysbiosis and bacterial killing in inflammatory bowel diseases," Guff Opin Infect Dis 22(3):292-301.

(56) References Cited

OTHER PUBLICATIONS

Palm et al., 'Immunoglobulin a Coating Identifies Colitogenic Bacteria in Inflammatory Bowel Disease', Cell, vol. 158, No. 5, pp. 1000-1010 (Aug. 28, 2014).
Peris-Bondia et al., 2011, "The active human gut microbiota differs from the total microbiota," PLoS One 6(7):e22448, doi: 10.1371/journal.pone.0022448. Epub Jul 28, 2011, 10 pages.
Peterson et al., 2007, IgA Response to Symbiotic Bacteria as a Mediator of Gut Homeostasis. Cell host & microbe 2:328. (12 pages).
Prindiville, Thomas P., et al., "Bacteroides fragilis Enterotoxin Gene Sequences in Patients with Inflammatory Bowel Disease", Emerging Infectious Diseases, vol. 6, No. 2, pp. 171-174. Apr. 1, 2000.
Rabizadeh et al., "Enterotoxigenic Bacteroides fragilis: A Potential Instigator of Colitis", Inflamm Bowel Dis, vol. 13, No. 12, pp. 1475-1483 (2007).
Rabizadeh, S., et al., "STAT3 Is Activated Throughout the Gastrointestinal Tract in Enterotoxigenic Bacteroides Fragilis Induces Colitis", Gastroenterology, vol. 134, No. 4, p. A-651. Apr. 1, 2008.
Rhee et al., "Induction of Persistent Colitis by a Human Commensal, Enterotoxigenic Bacteroides fragilis, in Wild-Type C57BU6 Mice", Infection and Immunity, vol. 77, No. 4, pp. 1708-1718 (2009).
Round and Mazmanian, 2009, "The gut microbiota shapes intestinal immune responses during health and disease," Nat Rev Immunol 9(5):313-323.
Saleh and Elson, 2011, "Experimental inflammatory bowel disease: insights into the host-microbiota dialog.," Immunity 34(3):293-302.
Salzman et al., 2002, Analysis of 16S libraries of mouse gastrointestinal microflora reveals a large new group of mouse intestinal bacteria. Microbiology, 148(11):3651-3660.
Sansonetti, 2011, "To be or not to be a pathogen: that is the mucosally relevant question," Mucosal Immunol 4(1):8-14.
Scher et al., 2013, "Expansion of intestinal Prevotella copri correlates with enhanced susceptibility to arthritis," Elife. Nov. 5, 2013;2:e01202. doi: 10.7554/eLife.01202. (20 pages).
Sears et al., "Association of Enterotoxigenic Bacteroides fragilis Infection with Inflammatory Diarrhea", Clin Infect Des, vol. 47, No. 6, pp. 797-803 (2008).
Sears. Cynthia L., "Enterotoxigenic Bacteroides fragilis: a Rogue among Symbiotes", Clinical Microbiology Reviews, Col. 22, No. 2, pp. 349-369. Apr. 1, 2009.
Shapiro et al., "Bridging the Gap Between Host Immune Response and Intestinal Dysbiosis in Inflammatory Bowel Disease: Does Immunoglobulin A Mark the Spot?" Clinical Gastroenterology and Hepatology 13(5):842-846 (2015).
Shinkura et al., 2004, "Separate domains of AID are required for somatic hypermutation and class-switch recombination," Nat Immunol 5:707-712.
Slack et al., 2012, Functional flexibility of intestinal IgA— broadening the fine line, Front. Immun. 3:100. (10 pages).
Stepankova et al., 2007, "Segmented filamentous bacteria in a defined bacterial cocktail induce intestinal inflammation in SCID mice reconstituted with CD45RBhigh CD4+ T cell," Inflamm Bowel Dis 13:1202-1211.
Strober, 2013, Impact of the gut microbiome on mucosal inflammation, Trends in immunology 34:423. (8 pages).
Strowig et al., 2012, Inflammasomes in health and disease. Nature 481:278-286.
Suzuki et al., 2004, Aberrant expansion of segmented filamentous bacteria in IgA-deficient gut. Proceedings of the National Academy of Sciences of the United States of America, 101:1981. (6 pages).
Talham et al., 1999, Segmented Filamentous Bacteria Are Potent Stimuli of a Physiologically Normal State of the Murine Gut Mucosal Immune System. Infection and Immunity 67:1992-2000.
Tezuka et al., 2007, "Regulation of IgA production by naturally occurring TNF/iNOS-producing dendritic cells," Nature 448(156):929-933.
Toprak, N., et al., "A possible role of Bacteroides fragilis enterotoxin in the aetiology of colorectal cancer", Clinical Microbiology and Infection, vol. 12, No. 8, p. 782-786. Aug. 1, 2006.
Toprak, N., et al., "The distribution of the bft alleles among enterotoxigenic *Bacteroides fragilis* strains from stool specimens and extraintestinal sites", Anaerobe, vol. 12, No. 2, pp. 71-74 (2005).
Tsuruta et al., 'The amount of secreted IgA may not determine the secretory IgA coating ratio of gastrointestinal', FEMS Immunology Med. Microbiology, vol. 56, No. 2, pp. 185-189 (May 7, 2009).
Tsuruta et al., "Development of a Method for the Identification of S-IgA-Coated Bacterial Composition in Mouse and Human Feces," Bioscience Biotechnology Biochemistry 74(5):968-973 (2010).
Umesaki et al., 1999, Differential Roles of Segmented Filamentous Bacteria and Clostridia in Development of the Intestinal Immune System. Infection and Immunity 67:3504-3511.
Van der Waaij et al., 1994, "Direct Flow Cytometry of Anaerobic Bacteria in Human Feces." Cytometry 16:270-279.
Van der Waaij et al., 1994, Direct Flow Cytometry of Anaerobic Bacteria in Human Feces. Cytometry 16:270.
Van Der Waaij, Laurens et al., 'Immunoglobulin coating of faecal bacteria in inflammatory bowel disease', European Journal of Gastroenterology & Hepatology, vol. 16, No. 7, pp. 669-674 (Jul. 2004 ).
Weiner et al., "Antibodies and cancer therapy: versatile platforms for cancer immunotherapy" Nat Rev Immunol May 2010; 10(5): 317-327.
Wirtz et al., "Mouse models of inflammatory bowel disease", Advaned Drug Delivery Reviews, vol. 59, No. 11, pp. 1073-1083 (2007).
Wu et al., 2010, Gut-Residing Segmented Filamentous Bacteria Drive Autoimmune Arthritis via T Helper 17 Cell Immunity 32:815, 13 pages.
Wu, S., et al., "A human colonic commensal promotes colon tumorigenesis via activation of T helper 17 T cell response", Nature Medicine, vol. 15, No. 9. p. 1016-1022. Sep. 1, 2009.
Zhang et al., 2009, Human gut microbiota in obesity and after gastric bypass. Proceedings of the National Academy of Sciences 106:2365. (6 pages).
International Search Report and Written Opinion issued by the International Searching Authority for Application No. PCT/US2019/040601, dated Oct. 8, 2019, 12 pages.

\* cited by examiner

Figure 6A
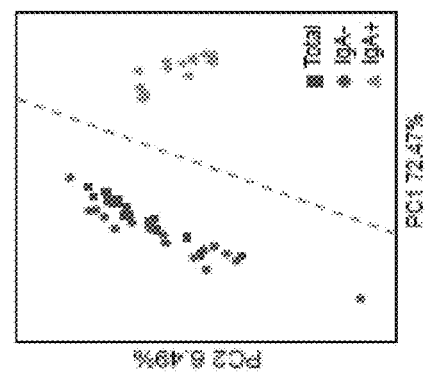
Figure 6B
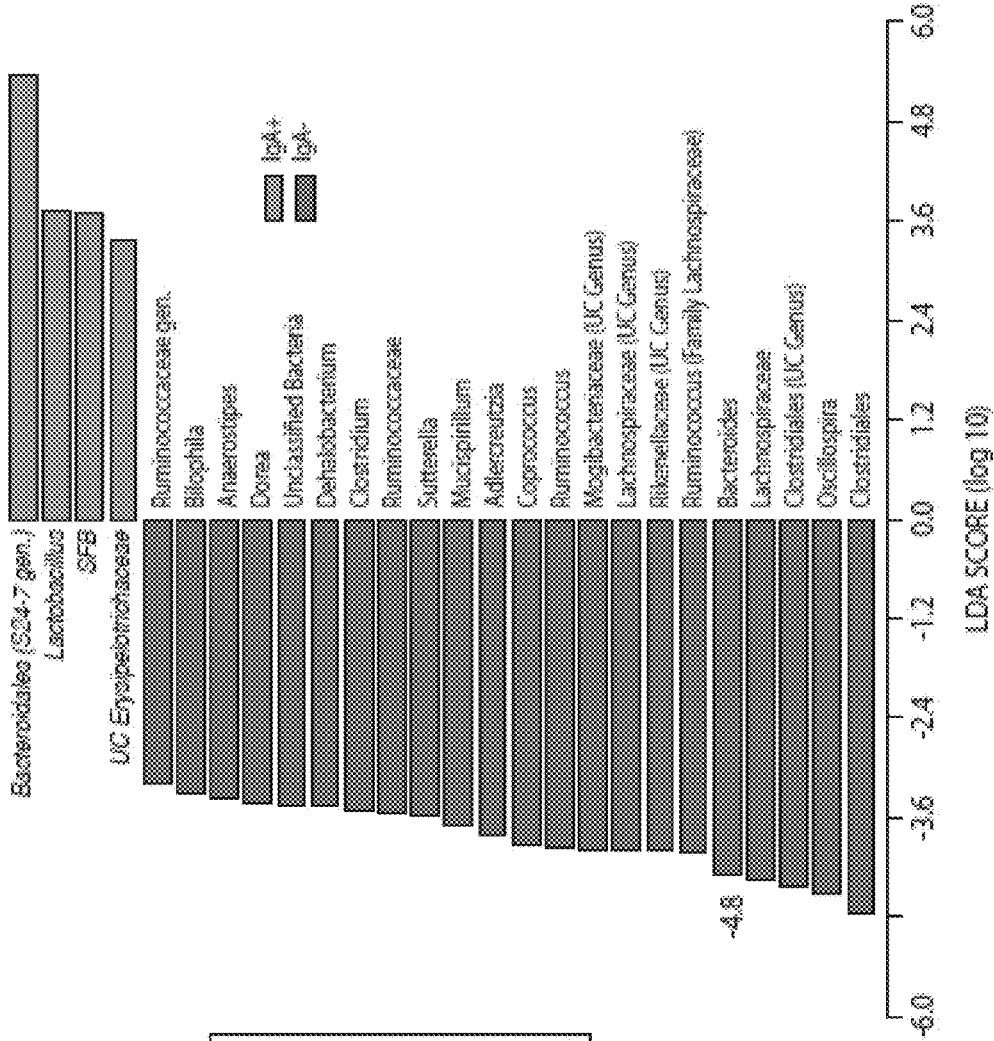
Figure 6

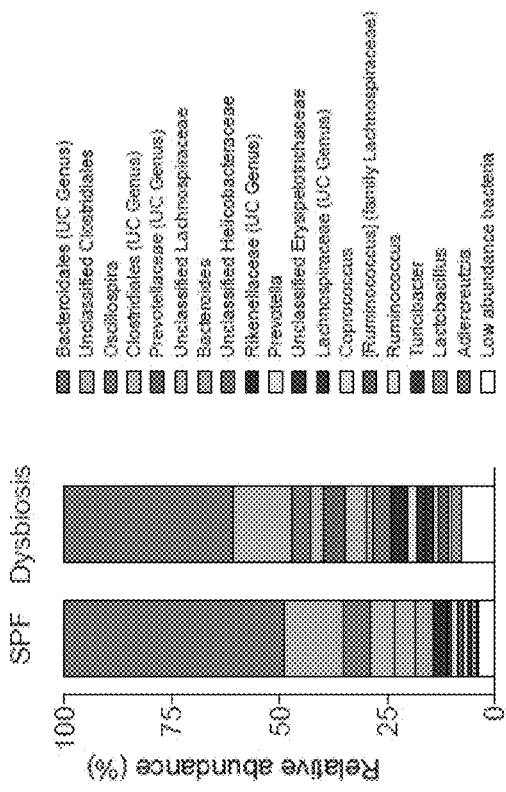
Figure 7A
Figure 7B
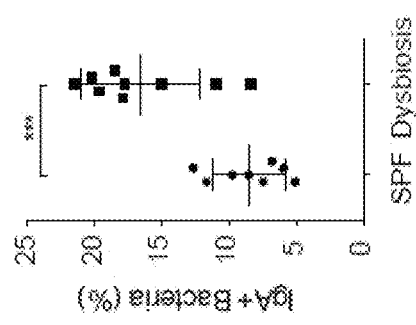
Figure 7D
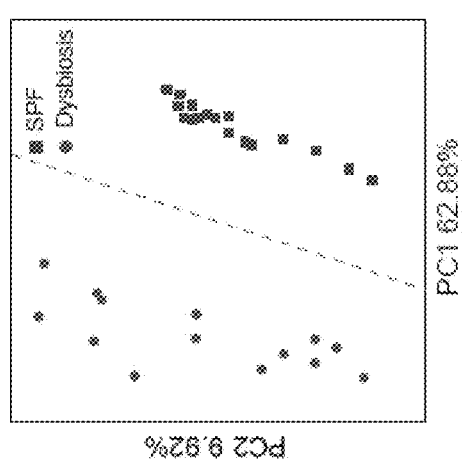
Figure 7C
Figure 7

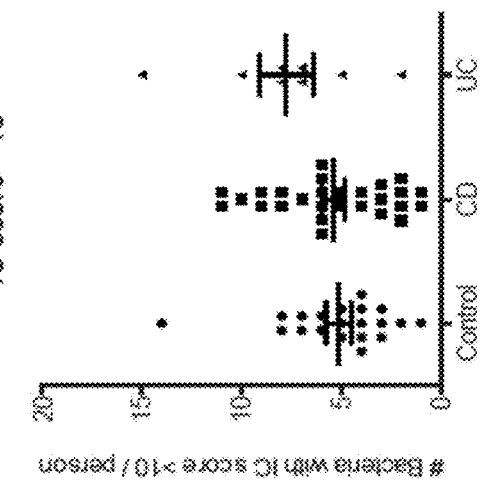
Figure 12A
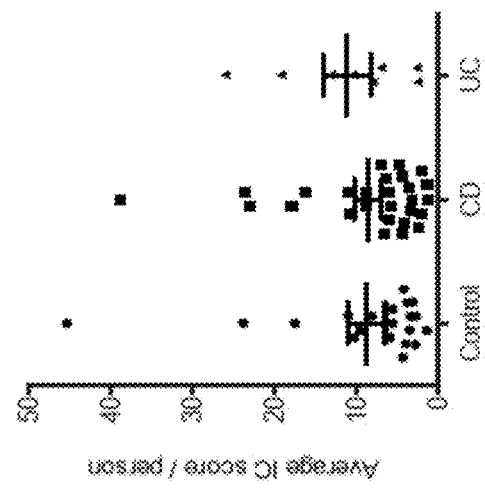
Figure 12B
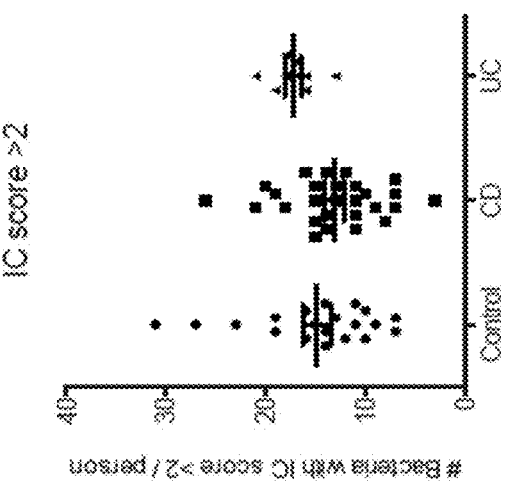
Figure 12C
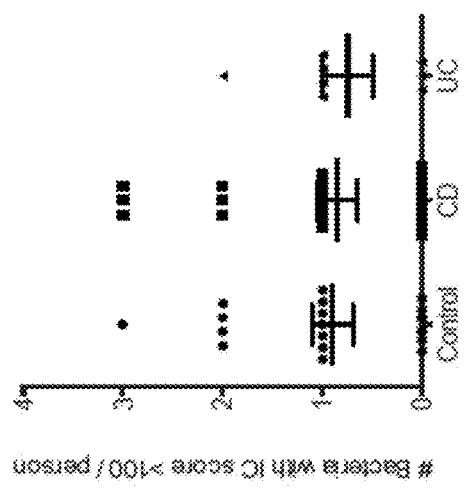
Figure 12D
Figure 12

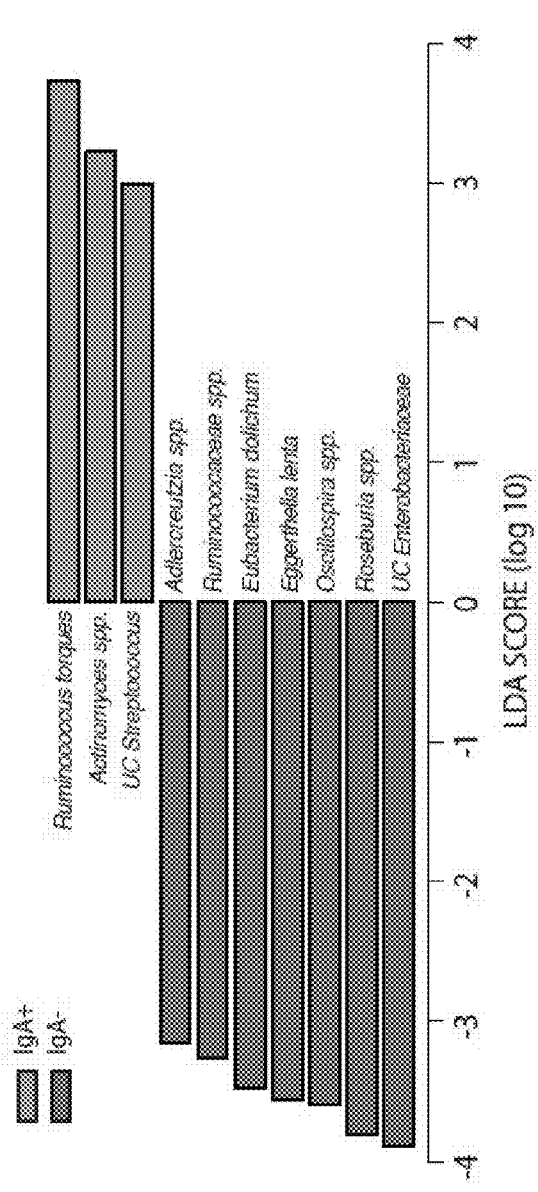
Figure 13B
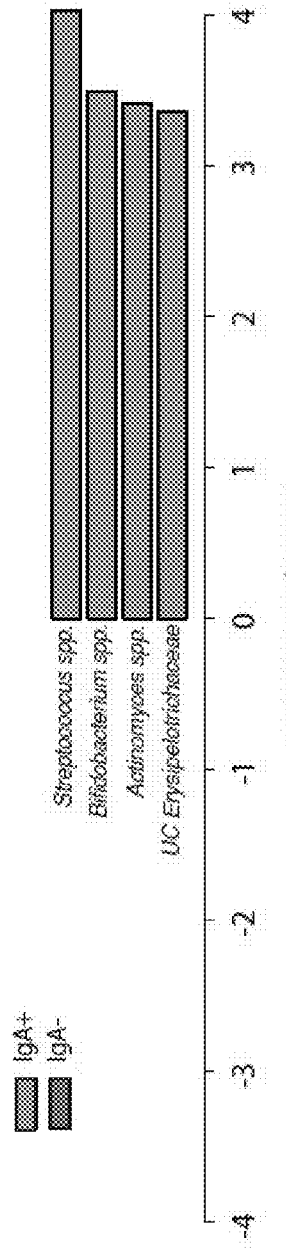
Figure 13C
Figure 13 (continued)

COMPOSITIONS AND METHODS FOR IDENTIFYING SECRETORY ANTIBODY-BOUND MICROBES

CROSS-REFERENCE TO RELATED APPLICATIONS

This application is a continuation of U.S. patent application Ser. No. 15/664,150, filed Jul. 31, 2017, which is a continuation of U.S. patent application Ser. No. 14/775,328, filed Sep. 11, 2015, which is the U.S. national stage application filed under 35 U.S.C. § 371 claiming benefit to International Patent Application No. PCT/US14/23967, filed Mar. 12, 2014, which is entitled to priority under 35 U.S.C. § 119(e) to U.S. Provisional Application No. 61/777,519, filed Mar. 12, 2013, each of which is hereby incorporated by reference in its entirety.

STATEMENT REGARDING FEDERALLY SPONSORED RESEARCH OR DEVELOPMENT

This invention was made with government support under grant number 2T32AR007107-37 awarded by the National Institutes of Health (NIH). The government has certain rights in the invention.

BACKGROUND OF THE INVENTION

The composition of the intestinal microbiota varies substantially between individuals and has dramatic effects on host physiology and disease susceptibility (Lozupone et al., 2012, Nature 489:220). A major mechanism by which the microbiota impacts the host is through its interactions with the intestinal immune system. Select members of the microbiota exert dramatic effects on the intestinal immune system and disease susceptibility through chronic stimulation of specific immune responses (Blumberg and Powrie, 2012, Science translational medicine 4:137rv7; Chow et al., 2011, Current opinion in immunology 23:473; Hooper et al., 2012, Science 336:1268; Littman and Pamer, Cell host & microbe 10:311), which can be both beneficial and detrimental. In mice, for example, Clostridia species induce the expansion of regulatory T cells and suppress allergic responses and intestinal inflammation (Atarashi et al., 2011, Science 331: 337), Segmented Filamentous Bacteria (SFB) induce T helper 17 responses, exacerbate the development of arthritis and protect against the development of diabetes (Wu et al., 2010, Immunity 32:815; Ivanov et al., 2009, Cell 139:485; Kriegel et al., 2011, Proceedings of the National Academy of Sciences of the United States of America 108:11548), and *Bacteroides fragilis* induces IL-10 production by T helper cells and ameliorates intestinal inflammation (Mazmanian et al., 2008, Nature 453:620).

Alterations in the composition of the microbiota, sometimes referred to as "dysbiosis," are known to drive development of both inflammatory and non-inflammatory diseases including inflammatory bowel disease, metabolic diseases, and autoimmunity (Littman and Pamer, 2011, Cell Host & Microbe 10:311-323). Crohn's disease is one such example, and it is characterized by chronic inflammation of the intestinal tract and affects millions of people worldwide (Abraham and Cho, 2009, New Engl. J. Med. 361:2066-2078). Although the exact cause of Crohn's disease is not known, members of the intestinal microbiota are believed to play a pivotal role in disease development. It is believed that many of these diseases and disorders are driven by specific members of the microbiota, which are referred to as "pathobionts."

Pathobionts are defined as bacteria present in the "normal" microbiota that have the potential to cause or drive disease development, and therefore share features with both commensal symbionts and pathogens (Chow et al., 2011, Curr. Opin. Immunol. 23:473-480). For example, Segmented Filamentous Bacteria (SFB) are common members of the mouse microbiota that exacerbate the development of autoimmunity (Wu et al., 2010, Immunity 32:815-827), and *Helicobacter* species drive the development of colitis in genetically susceptible mice. SFB and *Helicobacter* species therefore represent classical pathobionts.

Immunoglobulin A is the predominant antibody isotype secreted into the intestinal lumen where it binds indigenous members of the microbiota and controls microbiota composition (Macpherson 2012, Immunological reviews 245:132; Pabst, 2012, Nature Reviews Immunology; Suzuki et al., 2004, 101:1981; Peterson et al., 2007, Cell host & microbe 2:328). While all intestinal bacteria can induce specific IgA responses in principle (Hapfelmeier et al., 2010, Science 328:1705; Macpherson et al., 2000, Science 288:2222; Macpherson and Uhr, 2004, Science 303:1662), direct analyses of the proportion of intestinal bacteria that are coated with IgA demonstrated that only a fraction of all intestinal bacteria are measurably IgA coated (Tsuruta et al., 2009, FEMS immunology and medical microbiology 56:185; van der Waaij et al., 1996, Gut 38:348; van der Waaij et al., 1994, Cytometry 16:270). Because little is known about the specificity of the intestinal IgA response in the context of a complex microbiota, whether this fraction is comprised of many species or a high percentage of a few species remains unclear. However, while several commensal bacteria have been shown to induce specific IgA responses, pathobionts and pathogens induce higher levels of IgA than "true" commensals (Slack et al., 2012, Front. Immun. 3:100). For example, SFB and *Helicobacter* species are potent inducers IgA responses in the intestine (Umesaki et al., 1999, Infection and Immunity 67:3504-3511; Talham et al., 1999, Infection and Immunity 67:1992-2000). The inflammasome is a critical component of the innate immune system that orchestrates the activation of Caspase-1 and release of the inflammatory cytokines IL-1β and IL-18 in response to infection or damage. Mice lacking components of the inflammasome, such as the signaling adaptor apoptosis-associated speck-like protein containing a CARD (ASC), harbor a dysbiotic microbiota that is colitogenic and can be transmitted to wild type mice through co-housing (Strowig et al., 2012, Nature 481:278-286). In particular, acquisition of bacteria from the family Prevotellaceae has been implicated in colitis development in dysbiotic mice (Elinav et al., 2011, Cell 145:745-757).

Despite considerable effort, the identification of specific pathobionts responsible for driving the development of disease in humans has proven difficult due to the complexity and diversity of the microbiota, as well as the influence of host genetics and environment on disease susceptibility. Therefore, simple metagenomic studies comparing the microbiota of diseased and normal individuals may fail to identify disease-causing bacteria because these bacteria may be present in both groups, but only cause disease in a subset of susceptible individuals.

There is a need in the art to identify bacteria in the microbiota of a subject that can lead to the development or progression of diseases and disorders in the subject. The present invention addresses this unmet need.

SUMMARY OF THE INVENTION

The invention relates to the discovery that secretory antibodies can be used to detect and identify microbes present in the microbiota of a subject that influence susceptibility to or contribute to the development or progression of diseases or disorders, including inflammatory diseases and disorders. In one embodiment, the invention is a method of identifying a type of bacteria in the microbiota of a subject that contributes to the development or progression of an inflammatory disease or disorder in the subject, including the steps of: isolating secretory antibody-bound bacteria from the subject's biological sample, amplifying bacterial nucleic acid from secretory antibody-bound bacteria so isolated, determining the sequences of the amplicons, identifying the type of antibody-bound bacteria present in the subject's biological sample by identifying nucleic acid sequences that are indicative of particular types of bacteria. In some embodiments, the microbiota of the subject is on or near mucosal surface of the subject selected from the group consisting of the gastrointestinal tract, the respiratory tract, genitourinary tract and mammary gland. In some embodiments, the biological sample is at least one of a fecal sample, a mucus sample, a sputum sample, and a breast milk sample. In some embodiments, the bacterial nucleic acid is 16S rRNA. In some embodiments, the secretory antibody is at least one selected from the group consisting of IgA1, IgA2, and IgM. In some embodiments, the inflammatory disease or disorder is at least one inflammatory disease or disorder selected from the group consisting of inflammatory bowel disease, celiac disease, colitis, intestinal hyperplasia, metabolic syndrome, obesity, rheumatoid arthritis, liver disease, hepatic steatosis, fatty liver disease, non-alcoholic fatty liver disease (NAFLD), and non-alcoholic steatohepatitis (NASH). In some embodiments, the subject is human.

In another embodiment, the invention is a method of diagnosing an inflammatory disease or disorder in a subject in need thereof by identifying a type of bacteria in the microbiota of the subject that contributes to the development or progression of an inflammatory disease or disorder, including the steps of: isolating secretory antibody-bound bacteria from the subject's biological sample, amplifying bacterial nucleic acid from secretory antibody-bound bacteria so isolated, determining the sequences of the amplicons so amplified, and identifying the type of antibody-bound bacteria present in the subject's biological sample by identifying nucleic acid sequences that are indicative of particular types of bacteria, wherein when the type of antibody-bound bacteria present in the subject's biological sample is a type of bacteria that contributes to the development or progression of an inflammatory disease or disorder, the subject is diagnosed with the inflammatory disease or disorder. In some embodiments, the microbiota of the subject is on or near mucosal surface of the subject selected from the group consisting of the gastrointestinal tract, the respiratory tract, genitourinary tract and mammary gland. In some embodiments, the biological sample is at least one of a fecal sample, a mucus sample, a sputum sample, and a breast milk sample. In some embodiments, the bacterial nucleic acid is 16S rRNA. In some embodiments, the secretory antibody is at least one selected from the group consisting of IgA1, IgA2, and IgM. In some embodiments, the inflammatory disease or disorder is at least one inflammatory disease or disorder selected from the group consisting of inflammatory bowel disease, celiac disease, colitis, intestinal hyperplasia, metabolic syndrome, obesity, rheumatoid arthritis, liver disease, hepatic steatosis, fatty liver disease, non-alcoholic fatty liver disease (NAFLD), and non-alcoholic steatohepatitis (NASH). In some embodiments, the subject is human.

In one embodiment, the invention is a method of treating an inflammatory disease or disorder associated with a secretory antibody-bound bacteria in the microbiota of a subject in need thereof, the method comprising administering to the subject at least one therapy to diminish the number of at least one type of bacteria that is over-represented in the microbiota of the subject. In some embodiments, the at least one therapy is at least one selected from the group consisting of at least one vaccine, at least one antibiotic, and at least one passive immunotherapy. In some embodiments, the microbiota of the subject is on or near mucosal surface of the subject selected from the group consisting of the gastrointestinal tract, the respiratory tract, genitourinary tract and mammary gland. In some embodiments, the biological sample is at least one of a fecal sample, a mucus sample, a sputum sample, and a breast milk sample. In some embodiments, the secretory antibody is at least one selected from the group consisting of IgA1, IgA2, and IgM. In some embodiments, the inflammatory disease or disorder is at least one inflammatory disease or disorder selected from the group consisting of inflammatory bowel disease, celiac disease, colitis, intestinal hyperplasia, metabolic syndrome, obesity, rheumatoid arthritis, liver disease, hepatic steatosis, fatty liver disease, non-alcoholic fatty liver disease (NAFLD), and non-alcoholic steatohepatitis (NASH). In some embodiments, the subject is human. In some embodiments, the therapy induces an immune response directed against at least one type of secretory antibody-bound bacteria present in the microbiota of the subject. In some embodiments, the method further comprises administering to the subject at least one probiotic to increase the number of at least one type of bacteria under-represented in the microbiota of the subject.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1C, depicts the results of experiments demonstrating that IgA coating is uneven across microbial taxa. (FIG. 1A) Overview of IgA-based cell sorting of fecal bacteria combined with 16S rRNA sequencing (IgA-SEQ). (FIG. 1B) Representative cell sorting of IgA+ fecal bacteria from mice. A cartoon is used to illustrate separation of IgA+ and IgA− bacteria from total fecal bacteria. (FIG. 1C) Principal Coordinates Analysis of weighted UniFrac distances of Presort (total fecal bacteria), IgA+, IgA−, and mock-sorted (MACS and FACS) samples. PC, Principal Coordinate. PERMANOVA comparisons of weighted UniFrac distances of Presort, IgA+, IgA−, and mock-sorted samples demonstrated that IgA+ bacteria were phylogenetically distinct from Presort and IgA− fractions (P<0.05), while IgA− bacteria also were not significantly different from total bacteria (P=0.266). Mock sorting did not significantly alter the observed phylogenetic composition of fecal bacteria (Presort versus MACS: P=0.655; Presort versus FACS: P=0.606). Mock-sorted samples were stained with anti-IgA and sorted by MACS before mixing positive and negative fractions and FACS sorting of total bacteria.

FIGS. 2A-2B, depicts the results of experiments assessing IgA coating of fecal bacteria from Specific Pathogen Free (SPF) and SPF$^{dysbiosis}$ mice. Average relative abundances and IgA coating indices (ICI) for Total (Presort), IgA+ and IgA− bacterial genera from (FIG. 2A) C57Bl/6 SPF mice (n=17 samples) and (FIG. 2B) SPF$^{dysbiosis}$ mice (n=14 samples). SPF$^{dysbiosis}$ mice were co-housed with Asc$^{−/−}$ mice for at least 6 weeks to allow for the acquisition of dysbiosis. Relative abundance heatmaps are depicted on a logarithmic scale. Genera that are highly coated with IgA (significantly higher relative abundance in the IgA+ fraction as compared to the IgA− fraction by LEfSe (P<0.05) and Linear Discriminant Analysis Score>2), and Wilcoxon rank-sum (P<0.05)) are labeled in red (###), while genera that show low or no IgA coating (significantly higher relative abundance in the IgA− fraction as compared to the IgA+ fraction by LEfSe and Wilcoxon rank-sum) are labeled in blue (##).

FIGS. 3A-3C, depicts the results of experiments assessing IgA coating of fecal bacteria from healthy humans and inflammatory bowel disease patients. Depicted in the main heatmap are IgA coating index (ICI) scores for bacterial species from 20 healthy humans (FIG. 3A), 27 Crohn's disease patients (FIG. 3B), and 8 patients with UC (FIG. 3C). Each column represents an individual human subject. Bacterial taxa are clustered (complete linkage clustering using Euclidean distance) based ICI scores observed in healthy humans. Bacterial taxa with significantly higher relative abundance in the IgA+ fraction as compared to the IgA− fraction by LEfSe and Wilcoxon rank-sum are considered to be highly coated with IgA and are labeled in red (###). Bacterial taxa with significantly higher relative abundance in the IgA− fraction as compared to the IgA+ fraction by LEfSe and Wilcoxon rank-sum are considered to show low to no IgA coating and are labeled in blue (##). Bacterial taxa showing no significant difference in abundance in the IgA+ and IgA− fractions are labeled black. The leftmost heatmap summarizes the statistical comparisons between relative taxonomic abundance in the IgA+ and IgA− negative fraction. IgA coated bacteria are marked in red (###), low coated bacteria are marked in blue (##). Comparisons between ICI coating scores in Control and IBD patients are summarized as follows: gray marks no difference between diseased and control, green marks taxa where ICI scores are higher in controls than in diseased patients, and purple marks taxa where ICI scores are significantly lower in controls than in diseased patients. Significance levels for LEfSe and Wilcoxon rank-sum were P<0.05 and Linear Discriminant Analysis Score>2, and P<0.05, respectively.

FIGS. 4A-4B, depicts the results of experiments assessing IgA coating of fecal bacteria from SPF C57Bl/6 mice. (FIG. 4A) Staining of IgA coated intestinal bacteria from C57Bl/6 SPF and Rag2$^{−/−}$ mice, which lack immunoglobulins. (FIG. 4B) Gating on IgA− stained bacteria demonstrates that the vast majority of IgA+ events fall within the designated FSC and SSC gate. SSC, side scatter. FSC, forward scatter.

FIGS. 5A-4C, depicts the results of the sorting of IgA+ and IgA− fecal bacteria. (FIG. 5A) Post-sort purity of IgA+ and IgA− fractions. (FIG. 5B) IgA concentrations in total, IgA+ and IgA− bacterial fractions (after MACS sorting) as determined by whole bacterial-cell ELISA. (FIG. 5C) Average relative abundances of bacterial genera of >1% abundance in Presort (Total), IgA+, IgA−, and mock-sorted (MACS and FACS) samples (n=4 mice). UC, unclassified.

FIGS. 6A-6C, depicts the results of experiments assessing IgA coating of intestinal bacteria from SPF mice. (FIG. 6A) Principal Coordinate Analysis and PERMANOVA comparisons of weighted UniFrac distances of Total (Presort), IgA+ and IgA− fecal bacteria from SPF mice (n=17). PC, Principal Coordinate. (FIG. 6B) LEfSe comparisons of IgA+ and IgA− bacterial genera from SPF mice. (FIG. 6C) Relative abundance of bacterial families from total, IgA coated (IgA+) and noncoated (IgA−) intestinal bacteria from individual groups of SPF mice. Depicted are bacteria of >1% abundance as averaged from eight pairs of separately housed mice sampled at least two times. Significance levels for LEfSe were P<0.05 and Linear Discriminant Analysis Score>2. UC, unclassified.

FIG. 7, comprising FIGS. 7A-7D, depicts the results of experiments demonstrating that inflammasome-mediated dysbiosis leads to a hypersensitivity to DSS-induced colitis and increases the level of IgA coating of the microbiota. (FIG. 7A) Principal Coordinate Analysis of weighted UniFrac distances from SPF (n=17) and SPF$^{dysbiosis}$ mice (n=14). PERMANOVA P=0.001. (FIG. 7B) Average relative abundance of bacterial families in the intestinal microbiota from SPF and SPF$^{dysbiosis}$ mice. Prevotellaceae is marked with an arrow. UC, unclassified. (FIG. 7C) Dextran Sodium Sulfate (DSS)-induced colitis in SPF and SPF$^{dysbiosis}$ mice. Mice were treated with 2% DSS ad libitum in the drinking water for 7 days and weight was followed for 14 days. (FIG. 7D) IgA coating of fecal bacteria from SPF and SPF$^{dysbiosis}$ mice as measured by flow cytometry. SPF$^{dysbiosis}$ mice were co-housed with Asc$^{−/−}$ mice for at least 6 weeks to allow for the acquisition of dysbiosis. ***P<0.001 (unpaired Student's t-test).

FIGS. 8A-8C, depicts the results of experiments assessing IgA coating of intestinal bacteria from SPF$^{dysbiosis}$ mice. (FIG. 8A) Principal Coordinate Analysis and PERMANOVA comparisons of weighted UniFrac distances of Total (Presort), IgA+ and IgA− fecal bacteria from SPF (n=17) and SPF$^{dysbiosis}$ mice (n=14). PC, Principal Coordinate. (FIG. 8B) LEfSe comparisons of IgA+ and IgA− bacterial genera from SPF$^{dysbiosis}$ mice. (FIG. 8C) Relative abundance of bacterial families in total (Total), IgA coated (IgA+), and uncoated (IgA−) intestinal bacteria in SPF$^{dysbiosis}$ mice. Six pairs of separately housed dysbiotic mice (A-F) were sampled at least two times and the average of the two measurements is shown. Depicted are bacteria of >1% abundance. Significance levels for LEfSe were P<0.05 and Linear Discriminant Analysis Score>2. UC, unclassified.

FIGS. 11A-11C, depicts relative abundance heatmaps of intestinal bacteria from healthy humans, Crohn's disease patients, and patients with Ulcerative colitis. Relative abundance is depicted on a log scale to allow for visualization of low abundance taxa. Bacterial taxa are clustered (complete linkage clustering using Euclidean distance) based ICI scores observed in healthy humans.

Figure 3:
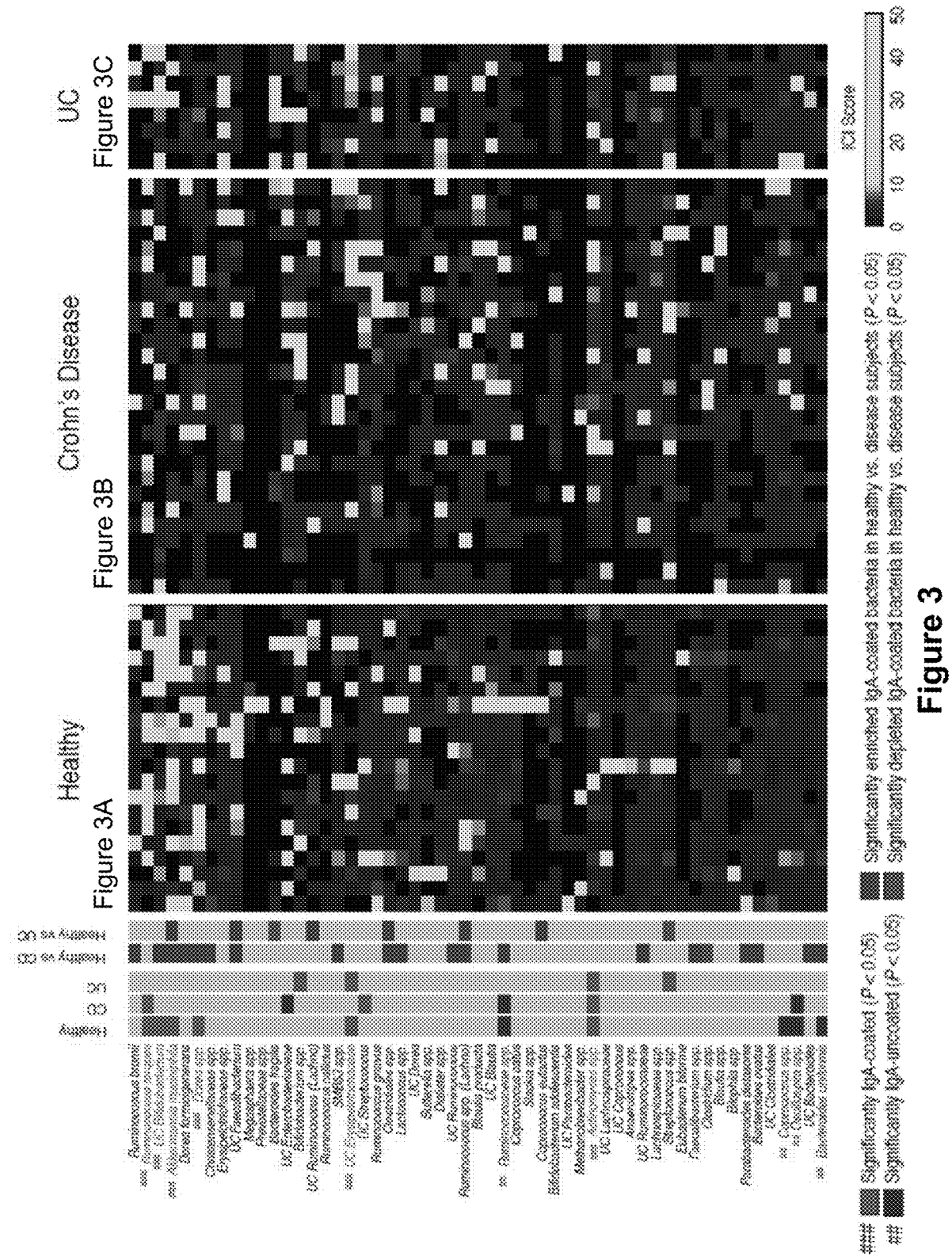
FIG. 3, comprising
Figure 3:
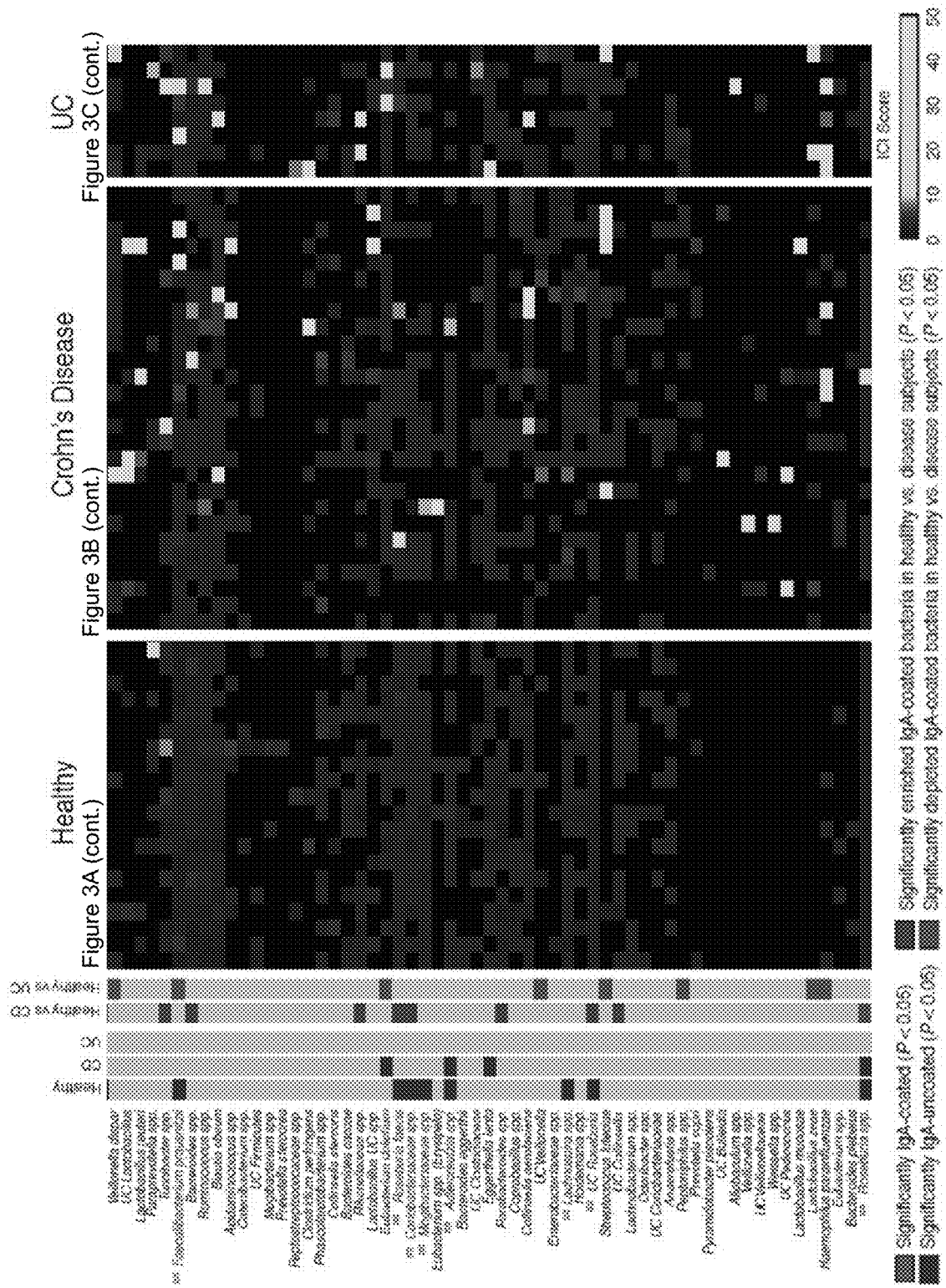

As in FIG. 3, bacterial taxa with significantly higher relative abundance in the IgA+ fraction as compared to the IgA− fraction by LEfSe and Wilcoxon rank-sum are considered to be highly coated with IgA and are labeled in red (###). Bacterial taxa with significantly higher relative abundance in the IgA− fraction as compared to the IgA+ fraction by LEfSe and Wilcoxon rank-sum are considered to show low to no IgA coating and are labeled in blue (##). Bacterial taxa showing no significant difference in abundance in the IgA+ and IgA− fractions are labeled black. Each column represents an individual human subject.

FIG. 12, comprising FIGS. 12A-12D, depicts the distributions of IgA coating index (ICI) scores in healthy humans and patients with Crohn's disease or Ulcerative colitis. (FIG. 12A-12C) Depicted are the number of IgA coated bacteria with an ICI score of >2, >10, and >100 in healthy humans and Crohn's disease or Ulcerative colitis patients. (FIG. 12D) Average ICI score per person.

Figures 13, 13A:
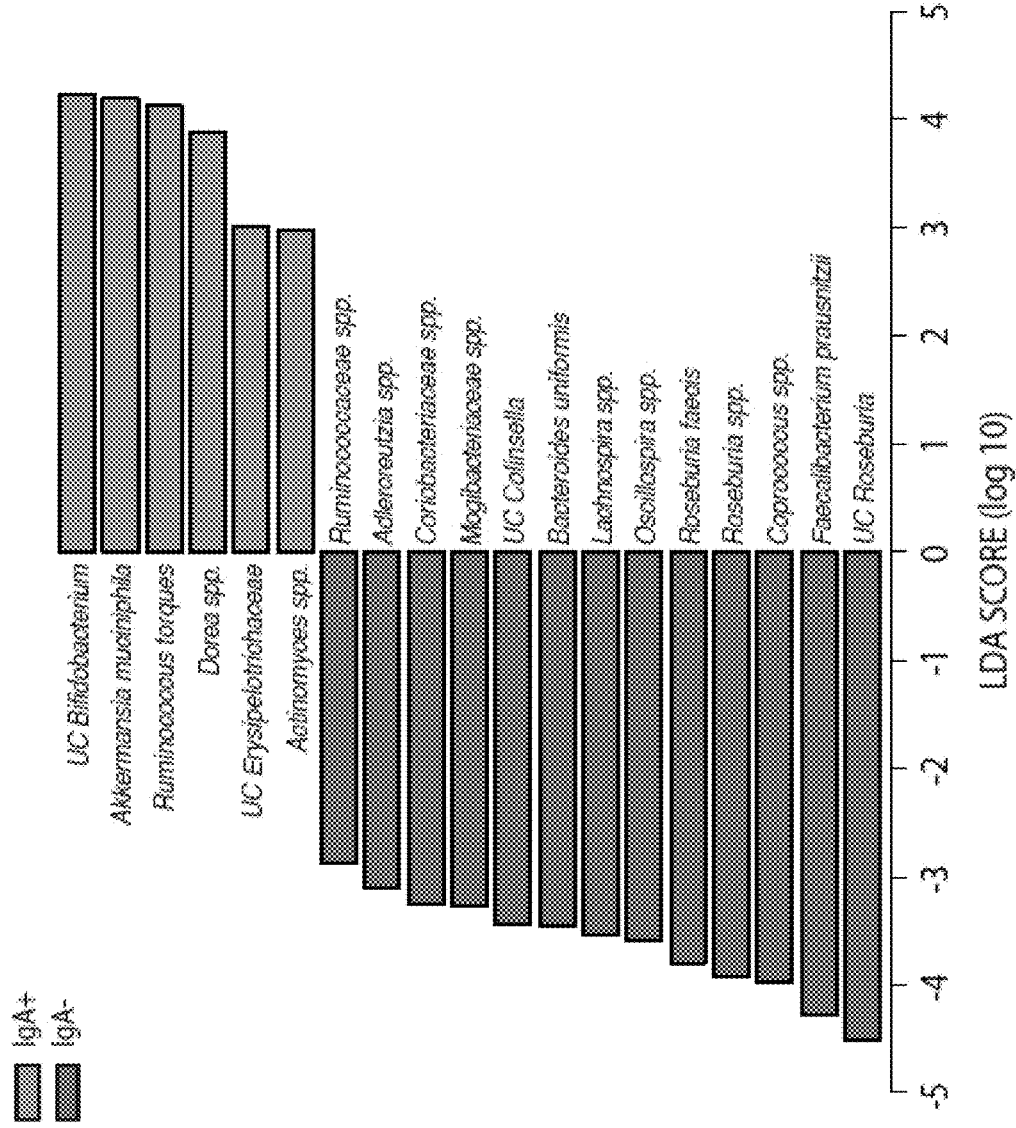

FIG. 13, comprising FIG. 13A-13C, depicts LEfSe comparisons of relative abundance of bacterial taxa from IgA+ and IgA− fractions of fecal bacteria from healthy humans and patients with Crohn's disease or Ulcerative Colitis. Bacterial taxa with significantly higher relative abundance in the IgA+ fraction as compared to the IgA− fraction by LEfSe are shown in green. Bacterial taxa with significantly higher relative abundance in the IgA− fraction as compared to the IgA+ fraction by LEfSe are shown in red. Bacterial taxa showing no significant difference in abundance in the IgA+ and IgA− fractions are omitted from these graphs. Significance levels for LEfSe were as follows: Kruskal-Wallis sum-rank P<0.05, Wilcoxon rank-sum P<0.05 and Linear Discriminant Analysis Score>2.

Figure 14:
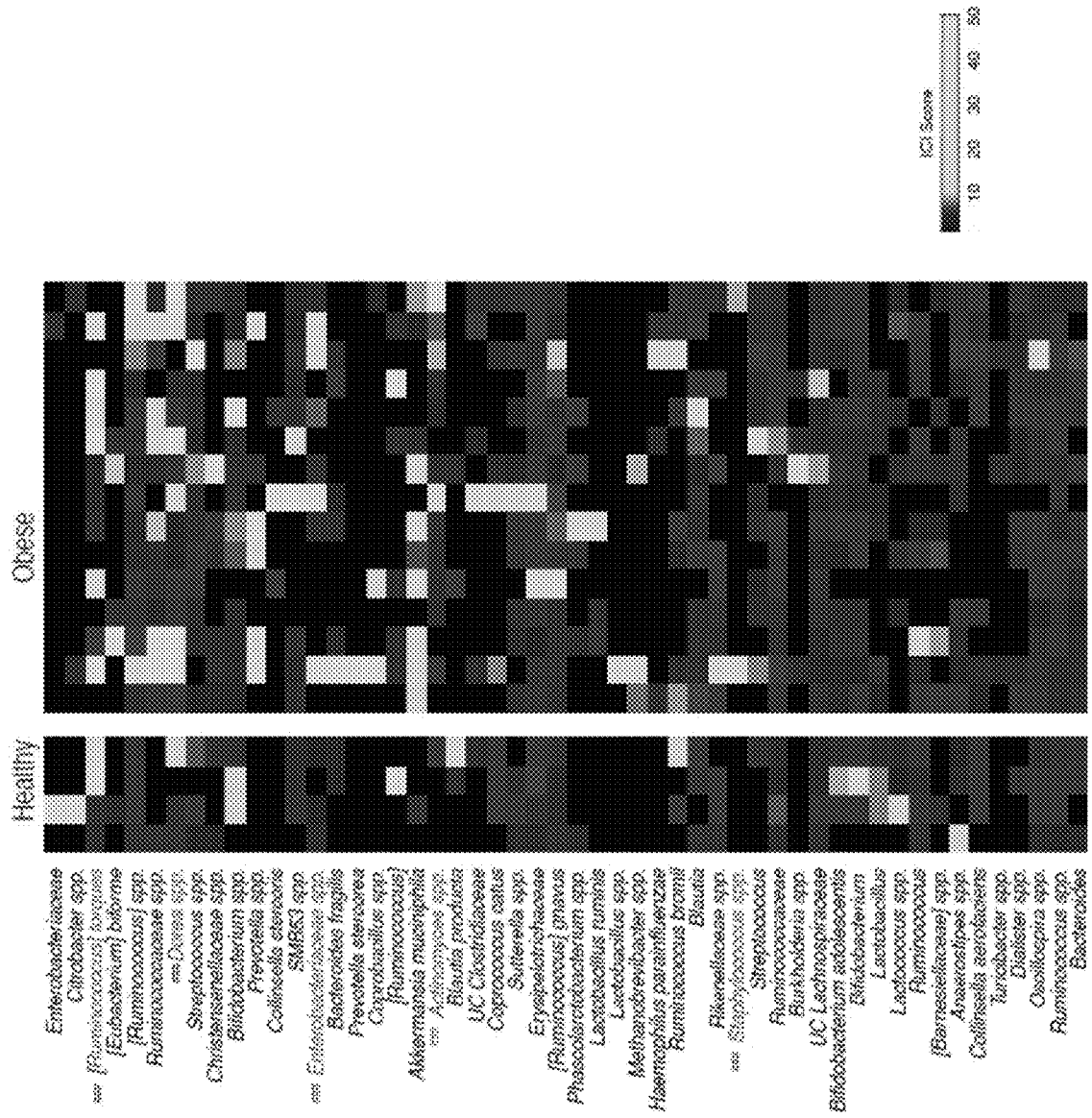
Figure 14:
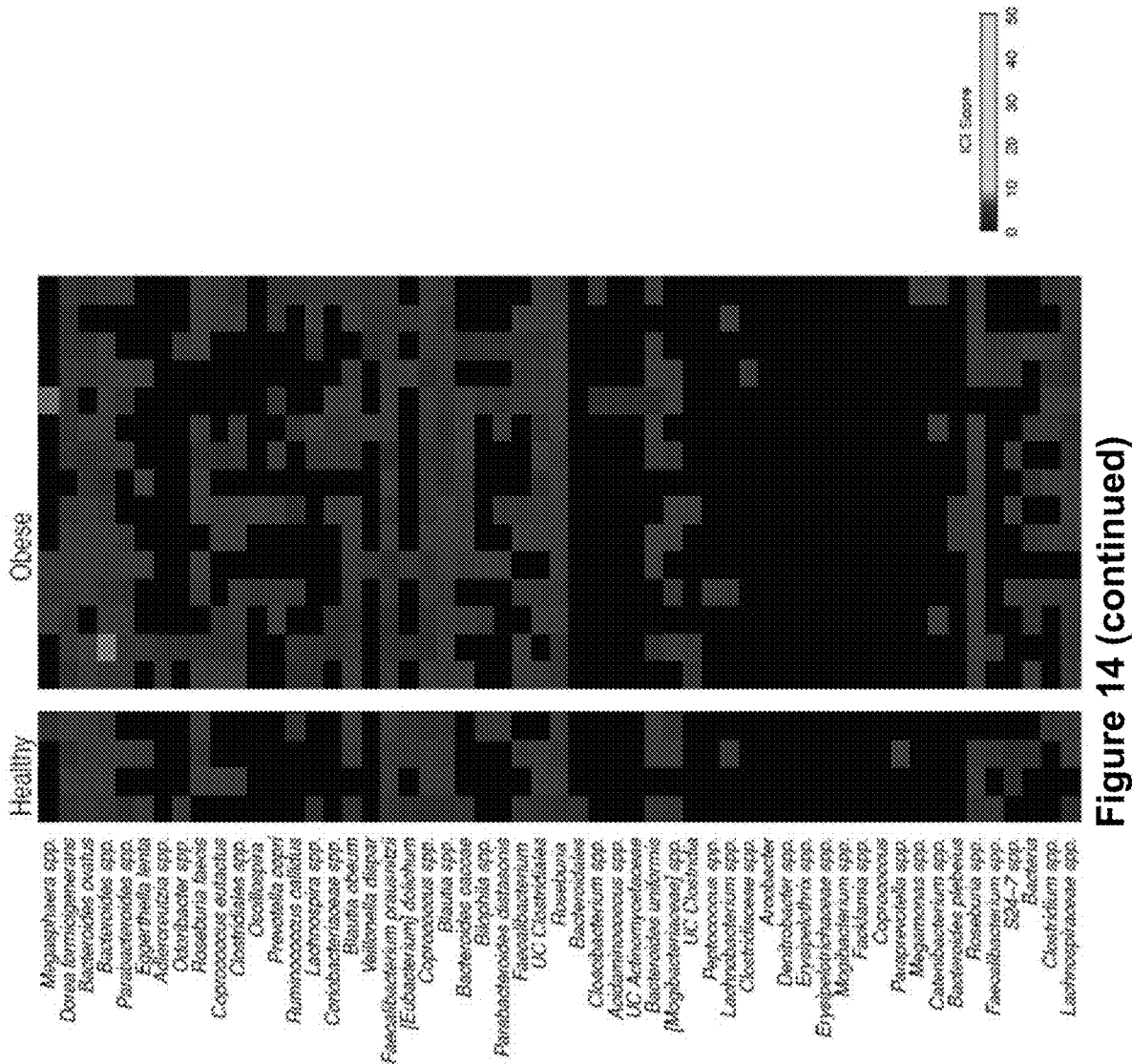

FIG. 14 depicts the results of experiments assessing the IgA coating of fecal bacteria from healthy and obese adolescents. Depicted in the main heatmap are IgA coating index (ICI) scores for bacterial species from 4 healthy and 15 obese adolescents. Each column represents an individual human subject. Bacterial taxa are clustered (complete linkage clustering using Euclidean distance) based ICI scores. Bacterial taxa from obese patients with significantly higher relative abundance in the IgA+ fraction as compared to the IgA− fraction by LEfSe are considered to be highly coated with IgA and are labeled in red (###).

DETAILED DESCRIPTION

The present invention relates to the discovery that secretory antibodies can be used to detect and identify microbes present in the microbiota of a subject that influence susceptibility to or contribute to the development or progression of diseases or disorders. Described herein are novel methods that combine flow cytometry-based microbial cell sorting and genetic analyses to detect, to isolate and to identify secretory antibody-coated (e.g., IgA-coated) microbes from the microbiota of a subject. Because disease-causing members of the microbiota, including pathobionts, are recognized by the subject's immune system, their presence triggers an immune response, including antibody production and secretion. In some embodiments of the methods described herein, the presence of an immune response (e.g., antibody production and secretion) in the subject serves as a marker and a means for isolating and identifying pathobionts, and putative pathobionts, that are the targets of the subject's immune response. Thus, the methods described herein can isolate and identify microbes present in the microbiota of a subject that influence susceptibility to or contribute to the development or progression of a disease or disorder. The microbiota of the subject can be any microbiota present on any mucosal surface of subject where antibody is secreted, including the gastrointestinal tract, the respiratory tract, genitourinary tract and mammary gland.

In various embodiments, the present invention relates to the isolation and identification of members of the microbiota that influence the development and progression of a disease or disorder, such as an inflammatory disease or disorder. Thus, the invention relates to compositions and methods for detecting and determining the identity of secretory antibody-coated constituents of a subject's microbiota to determine whether the secretory antibody-coated constituents of a subject's microbiota contribute to an altered microbiota associated with an inflammatory disease or disorder. In various embodiments, the relative proportions of the secretory antibody-coated and uncoated constituents of a subject's microbiota are indicative of an altered microbiota associated with an inflammatory disease or disorder. In some embodiments, the detection and identification of secretory antibody-coated constituents of the microbiota of the subject are used to diagnose the subject as having, or as at risk of developing, an inflammatory disease or disorder. Thus, in some embodiments, the altered microbiota of a subject influences susceptibility to or contributes to the development or progression of a disease or disorder, such as an inflammatory disease or disorder. In various embodiments, the inflammatory diseases and disorders associated with altered microbiota having secretory antibody-coated constituents include, but are not limited to, at least one of: inflammatory bowel disease, celiac disease, colitis, intestinal hyperplasia, metabolic syndrome, obesity, rheumatoid arthritis, liver disease, hepatic steatosis, fatty liver disease, non-alcoholic fatty liver disease (NAFLD), or non-alcoholic steatohepatitis (NASH).

Further, the present invention relates to methods of modifying an altered microbiota having secretory antibody-coated constituents in a subject in need thereof. In some embodiments, the invention provides compositions and methods for supplementing constituents of an altered microbiota that are under-represented in the altered microbiota, as compared with a normal microbiota, to restore the subject's microbiota to a normal microbiota. In other embodiments, the invention provides compositions and methods for diminishing constituents of an altered microbiota that are over-represented in the altered microbiota as compared with a normal microbiota, such as over-represented secretory antibody-coated constituents, to restore the subject's microbiota to a normal microbiota. In further embodiments, the invention provides compositions and methods for both supplementing constituents of an altered microbiota that are under-represented in the altered microbiota, as well as diminishing constituents of an altered microbiota that are over-represented in the altered microbiota, as compared with a normal microbiota, to restore the subject's microbiota to a normal microbiota.

As used throughout herein, constituents of an altered microbiota that are over-represented in the altered microbiota as compared with a normal microbiota, include constituents that are uniquely present in the altered microbiota as compared with a normal microbiota.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "dysbiosis," as used herein, refers to imbalances in quality, absolute quantity, or relative quantity of members of the microbiota of a subject, which is sometimes, but not necessarily, associated with the development or progression of a disease or disorder.

The term "microbiota," as used herein, refers to the population of microorganisms present within or upon a subject. The microbiota of a subject includes commensal microorganisms found in the absence of disease and may also include pathobionts and disease-causing microorganisms found in subjects with or without a disease or disorder.

The term "pathobiont," as used herein, refers to potentially disease-causing members of the microbioata that are present in the microbiota of a non-diseased or a diseased subject, and which has the potential to contribute to the development or progression of a disease or disorder.

An "effective amount" or "therapeutically effective amount" of a compound is that amount of a compound which is sufficient to provide a beneficial effect to the subject to which the compound is administered.

As used herein, an "instructional material" includes a publication, a recording, a diagram, or any other medium of expression which can be used to communicate the usefulness of a compound, composition, or method of the invention in a kit. The instructional material of the kit of the invention can, for example, be affixed to a container which contains the identified compound, composition, or method of the invention or be shipped together with a container which contains the identified compound, composition, or method of the invention. Alternatively, the instructional material can be shipped separately from the container with the intention that the instructional material and the compound, composition, or method of the invention be used cooperatively by the recipient.

The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

The terms "patient," "subject," "individual," and the like are used interchangeably herein, and refer to any animal, or cells thereof whether in vitro or in vivo, amenable to the methods described herein. In certain non-limiting embodiments, the patient, subject or individual is, by way of non-limiting examples, a human, a dog, a cat, a horse, or other domestic mammal.

A "therapeutic" treatment is a treatment administered to a subject who exhibits signs or symptoms of pathology, for the purpose of diminishing or eliminating those signs or symptoms.

As used herein, "treating a disease or disorder" means reducing the severity and/or frequency with which a sign or symptom of the disease or disorder is experienced by a patient. Disease and disorder are used interchangeably herein.

The phrase "biological sample" as used herein, is intended to include any sample comprising a cell, a tissue, feces, or a bodily fluid in which the presence of a microbe, nucleic acid or polypeptide is present or can be detected. Samples that are liquid in nature are referred to herein as "bodily fluids." Biological samples may be obtained from a patient by a variety of techniques including, for example, by scraping or swabbing an area of the subject or by using a needle to obtain bodily fluids. Methods for collecting various body samples are well known in the art.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes and binds to a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "probiotic" refers to one or more bacteria that can be administered to a subject to aid in the restoration of a subject's microbiota by increasing the number of bacteria that are under-represented in the subject's microbiota.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the discovery that secretory antibodies, such as IgA1, IgA2 or IgM, can be used to detect and identify microbes present in the microbiota of a subject that influence susceptibility to or contribute to the development or progression of a diseases or disorder, such as an inflammatory disease or disorder. Thus, the invention relates to compositions and methods for detecting, identifying and determining the absolute number or relative proportions of the secretory antibody-coated and uncoated constituents of a subject's microbiota, to determine whether a subject's microbiota is an altered microbiota associated with a disease or disorder, such as an inflammatory disease or disorder. Further, the present invention relates to methods of modifying an altered microbiota population in a subject in need thereof. The microbiota of the subject can be any microbiota present on any mucosal surface of subject where antibody is secreted, including the gastrointestinal tract, the respiratory tract, genitourinary tract and mammary gland.

Methods of Identifying

The methods of the invention are useful for detecting, identifying and determining the absolute number or relative proportions of secretory antibody-coated and uncoated constituents of a subject's microbiota, to determine whether a subject's microbiota is an altered microbiota associated with a disease or disorder, such as an inflammatory disease or disorder. In some embodiments, the methods of the invention combine a flow cytometry-based microbial cell sorting and genetic analyses to detect, to isolate and to identify secretory antibody-coated microbes from the microbiota of a subject. Pathobionts, as well as other disease-causing microbes, present in the microbiota of the of the subject are recognized by the subject's immune system, which triggers an immune response, including antibody production and secretion, directed against the pathobionts, and disease-causing microbes. Thus, in some embodiments of the methods of the invention, specifically binding secretory antibodies (e.g., IgA, IgM) produced by the subject and secreted through the mucosa of the subject, serve as a marker and a means for isolating and identifying putative pathobionts, pathobionts, and other disease-causing bacteria, that are the targets of the subject's immune response. In various embodiments of the methods of the invention, the secretory antibody is IgA (i.e., IgA1, IgA2), or IgM, or any combination thereof. The microbiota of the subject can be any microbiota present on any mucosal surface of subject where antibody is secreted, including the gastrointestinal tract, the respiratory tract, genitourinary tract and mammary gland.

In various embodiments, the present invention relates to the isolation and identification of constituents of the microbiota of a subject that influence the development and progression of a disease or disorder, such as an inflammatory disease and disorder. In one embodiment, the invention relates to compositions and methods for detecting and determining the identity of secretory antibody-coated constituents of a subject's microbiota to determine whether the secretory antibody-coated constituents of a subject's microbiota form an altered microbiota associated with an inflammatory disease or disorder. In various embodiments, the relative proportions of the secretory antibody-coated and uncoated constituents of a subject's microbiota are indicative of an altered microbiota associated with an inflammatory disease or disorder. In some embodiments, the detection and identification of secretory antibody-coated constituents of the microbiota of the subject are used to diagnose the subject as having, or as at risk of developing, an inflammatory disease or disorder. In other embodiments, the detection and identification of secretory antibody-coated constituents of the microbiota of the subject are used to diagnose the subject as having, or as at risk of developing, a recurrence or flare of an inflammatory disease or disorder. In other embodiments, the detection and identification of secretory antibody-coated constituents of the microbiota of the subject are used to diagnose the subject as having, or as likely to have, remission or an inflammatory disease or disorder. In various embodiments, the inflammatory diseases and disorders associated with altered microbiota having secretory antibody-coated constituents include, but are not limited to, at least one of: inflammatory bowel disease, celiac disease, colitis, intestinal hyperplasia, metabolic syndrome, obesity, rheumatoid arthritis, liver disease, hepatic steatosis, fatty liver disease, non-alcoholic fatty liver disease (NAFLD), or non-alcoholic steatohepatitis (NASH).

In one embodiment, the invention is a method for determining the relative proportions of the types of secretory antibody-coated constituents of a subject's microbiota, to identify constituents of a subject's microbiota that are associated with the development or progression of an inflammatory disease or disorder. In some embodiments, the detection of particular types of secretory antibody-coated constituents of the subject's microbiota is used to diagnose the subject as having, or as at risk of developing, an inflammatory disease or disorder. In various embodiments, the inflammatory disease or disorder associated with secretory antibody-coated constituents of the subject's microbiota include, but are not limited to, at least one of: inflammatory bowel disease, celiac disease, colitis, intestinal hyperplasia, metabolic syndrome, obesity, rheumatoid arthritis, liver disease, hepatic steatosis, fatty liver disease, non-alcoholic fatty liver disease (NAFLD), and non-alcoholic steatohepatitis (NASH). In some embodiments, the secretory antibody-coated constituent of the subject's microbiota associated with the develop or progression of an inflammatory disease or disorder in the subject is a Segmented Filamentous Bacteria (SFB) or *Helicobacter flexispira*. In other embodiments, the secretory antibody-coated constituent of the subject's microbiota associated with the development or progression of an inflammatory disease or disorder in the subject is a bacteria from a family selected from the group consisting of *Lactobacillus, Helicobacter*, S24-7, Erysipelotrichaceae and Prevotellaceae. In some embodiments, the bacteria from the family Prevotellaceae is a bacteria from the genera of *Paraprevotella* or *Prevotella*. In other embodiments, the secretory antibody-coated constituent of the subject's microbiota associated with the development or progression of an inflammatory disease or disorder in the subject is at least one selected from *Eubacterium, Eubacterium biforme, Eubacterium dolichum, Ruminococcus gnavus, Acidaminococcus, Actinomyces, Allobaculum, Anaerostipes, Bacteroides, Bacteroides fragilis, Bacteroides* Other, *Bifidobacterium, Bifidobacterium adolescentis, Bifidobacterium* Other, *Blautia, Blautia obeum, Blautia* Other, *Blautia producta, Bulleidia* Other, *Clostridium, Clostridium perfringens, Collinsella aerofaciens, Coprococcus, Coprococcus catus, Dialister, Eggerthella lenta,* Erysipelotrichaceae, *Faecalibacterium prausnitzii, Haemophilus parainfluenzae,* Lachnospiraceae, Lachnospiraceae other, *Lactobacillus, Lactobacillus mucosae, Lactobacillus* Other, *Lactobacillus reuteri, Lactobacillus zeae, Oscillospira, Pediococcus* Other, Rikenellaceae, *Roseburia, Roseburia faecis,* Ruminococcaceae, *Ruminococcus, Ruminococcus bromii,* SMB53, *Streptococcus, Streptococcus luteciae, Streptococcus* Other, *Sutterella, Turicibacter,* UC Clostridiales, UC Erysipelotrichaceae, UC Ruminococcaceae, *Veillonella, Veillonella dispar,* and *Weissella.*

In some embodiments, the invention is a method of identifying the type or types of secretory antibody-bound bacteria present in the microbiota of a subject that contribute to the development or progression of an inflammatory disease or disorder in the subject. In other embodiments, the invention is a method of diagnosing an inflammatory disease or disorder in a subject by identifying a type or types of secretory antibody-bound bacteria in the microbiota of the subject that contribute to the development or progression of an inflammatory disease or disorder.

Specific alterations in a subject's microbiota, including the presence of secretory antibody-coated constituents, can be detected using various methods, including without limitation quantitative PCR or high-throughput sequencing methods which detect relative proportions of microbial genetic markers in a total heterogeneous microbial population. In some embodiments, the microbial genetic marker is a bacterial genetic marker. In particular embodiments, the bacterial genetic marker is at least some portion of the 16S rRNA. In some embodiments, the relative proportion of particular constituent bacterial phyla, classes, orders, families, genera, and species present in the microbiota of a subject is determined. In other embodiments, the relative proportion of secretory antibody-coated and/or uncoated constituent bacterial phyla, classes, orders, families, genera, and species present in the microbiota of a subject is determined. In some embodiments, the relative proportion of particular constituent bacterial phyla, classes, orders, families, genera, and species present in the microbiota of a subject is determined and compared with that of a comparator normal microbiota. In other embodiments, the relative proportion of secretory antibody-coated and/or uncoated constituent bacterial phyla, classes, orders, families, genera, and species present in the microbiota of a subject is determined and compared with that of a comparator normal microbiota. In various embodiments, the comparator normal microbiota is, by way of non-limiting examples, a microbiota of a subject known to be free of an inflammatory disorder, or ahistorical norm, or a typical microbiota of the population of which the subject is a member.

In one embodiment, the method of the invention is a diagnostic assay for diagnosing an inflammatory disease or disorder associated with an altered microbiota in a subject in need thereof, by determining the absolute or relative abundance of particular types of secretory antibody-coated constituents of the subject's microbiota present in a biological sample derived from the subject. In some embodiments, the subject is diagnosed as having an inflammatory disease or disorder when particular types of secretory antibody-coated bacteria are determined to be present in the biological sample derived from the subject with increased relative abundance. In some embodiments, the secretory antibody-coated bacteria determined to be present in the biological sample derived from the subject with increased relative abundance is a Segmented Filamentous Bacteria (SFB) or *Helicobacter flexispira.* In some embodiments, the secretory antibody-coated bacteria determined to be present in the biological sample derived from the subject with increased relative abundance is a bacteria from a family selected from the group consisting of *Lactobacillus, Helicobacter,* S24-7, Erysipelotrichaceae and Prevotellaceae. In some embodiments, the bacteria from the family Prevotellaceae is a bacteria from the genera of *Paraprevotella* or *Prevotella.* In other embodiments, the secretory antibody-coated constituent of the subject's microbiota associated with the development or progression of an inflammatory disease or disorder in the subject is at least one selected from *Eubacterium, Eubacterium biforme, Eubacterium dolichum, Ruminococcus gnavus, Acidaminococcus, Actinomyces, Allobaculum, Anaerostipes, Bacteroides, Bacteroides fragilis, Bacteroides* Other, *Bifidobacterium, Bifidobacterium adolescentis, Bifidobacterium* Other, *Blautia, Blautia obeum, Blautia* Other, *Blautia producta, Bulleidia* Other, *Clostridium, Clostridium perfringens, Collinsella aerofaciens, Coprococcus, Coprococcus catus, Dialister, Eggerthella lenta,* Erysipelotrichaceae, *Faecalibacterium prausnitzii, Haemophilus parainfluenzae,* Lachnospiraceae, Lachnospiraceae other, *Lactobacillus, Lactobacillus mucosae, Lactobacillus* Other, *Lactobacillus reuteri, Lactobacillus zeae, Oscillospira, Pediococcus* Other, Rikenellaceae, *Roseburia, Roseburia faecis,* Ruminococcaceae, *Ruminococcus, Ruminococcus bromii,* SMB53, *Streptococcus, Streptococcus luteciae, Streptococcus* Other, *Sutterella, Turicibacter,* UC Clostridiales, UC Erysipelotrichaceae, UC Ruminococcaceae, *Veillonella, Veillonella dispar,* and *Weissella.*

The results of the diagnostic assay can be used alone, or in combination with other information from the subject, or from the biological sample derived from the subject.

In the assay methods of the invention, a test biological sample from a subject is assessed for the absolute or relative abundance of secretory antibody-coated and uncoated constituents of the microbiota. The test biological sample can be an in vitro sample or an in vivo sample. In various embodiments, the subject is a human subject, and may be of any race, sex and age. Representative subjects include those who are suspected of having an altered microbiota associated with an inflammatory disease or disorder, those who have been diagnosed with an altered microbiota associated with an inflammatory disease or disorder, those whose have an altered microbiota associated with an inflammatory disease or disorder, those who have had an altered microbiota associated with an inflammatory disease or disorder, those who at risk of a recurrence of an altered microbiota associated with an inflammatory disease or disorder, those who at risk of a flare of an altered microbiota associated with an inflammatory disease or disorder, and those who are at risk of developing an altered microbiota associated with an inflammatory disease or disorder.

In some embodiments, the test sample is prepared from a biological sample obtained from the subject. In some instances, a heterogeneous population of microbes will be present in the biological samples. Enrichment of a microbial population for microbes (e.g., bacteria) bound by secretory antibody (e.g., IgA, IgM) may be accomplished using separation technique. For example, microbes of interest may be enriched by separation the microbes of interest from the initial population using affinity separation techniques. Techniques for affinity separation may include magnetic separation using magnetic beads conjugated with an affinity reagent, affinity chromatography, "panning" with an affinity reagent attached to a solid matrix, e.g. plate, or other convenient technique. Other techniques providing separation include fluorescence activated cell sorting, which can have varying degrees of sophistication, such as multiple color channels, low angle and obtuse light scattering detecting channels, impedance channels, etc. One example of an affinity reagent useful in the methods of the invention is an antibody, such as anti-species antibody or anti-isotype (e.g., anti-IgA, anti-IgM) antibody. The details of the preparation of such antibodies and their suitability for use as affinity reagents are well-known to those skilled in the art. In some embodiments, labeled antibodies are used as affinity reagents. Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type.

In various embodiments, the initial population of microbes is contacted with one or more affinity reagent(s) and incubated for a period of time sufficient to permit the affinity reagent to specifically bind to its target. The microbes in the contacted population that become labeled by the affinity reagent are selected for by any convenient affinity separation technique, e.g. as described elsewhere herein or as known in the art. Compositions highly enriched for a microbe of interest (e.g., secretory antibody-bound bacteria) are achieved in this manner. The affinity enriched microbes will be about 70%, about 75%, about 80%, about 85% about 90%, about 95% or more of the composition. In other words, the enriched composition can be a substantially pure composition of the microbes of interest.

In one embodiment, the test sample is a sample containing at least a fragment of a bacterial nucleic acid. The term, "fragment," as used herein, indicates that the portion of a nucleic acid (e.g., DNA, RNA) that is sufficient to identify it as comprising a bacterial nucleic acid.

In some embodiments, the test sample is prepared from a biological sample obtained from the subject. The biological sample can be a sample from any source which contains a bacterial nucleic acid (e.g., DNA, RNA), such as a bodily fluid or fecal sample, or a combination thereof. A biological sample can be obtained by any suitable method. In some embodiments, a biological sample containing bacterial DNA is used. In other embodiments, a biological sample containing bacterial RNA is used. The biological sample can be used as the test sample; alternatively, the biological sample can be processed to enhance access to nucleic acids, or copies of nucleic acids, and the processed biological sample can then be used as the test sample. For example, in various embodiments, nucleic acid is prepared from a biological sample, for use in the methods. Alternatively or in addition, if desired, an amplification method can be used to amplify nucleic acids comprising all or a fragment of an RNA or DNA in a biological sample, for use as the test sample in the assessment of the presence, absence and proportion of particular types of bacteria present in the sample.

In some embodiments, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of nucleic acid from a particular type of bacteria can be determined by hybridization of nucleic acid to a nucleic acid probe. A "nucleic acid probe," as used herein, can be a DNA probe or an RNA probe.

The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target RNA or DNA. The hybridization sample is maintained under conditions which are sufficient to allow specific hybridization of the nucleic acid probe to RNA or DNA. Specific hybridization can be performed under high stringency conditions or moderate stringency conditions, as appropriate. In a preferred embodiment, the hybridization conditions for specific hybridization are high stringency. More than one nucleic acid probe can also be used concurrently in this method. Specific hybridization of any one of the nucleic acid probes is indicative of the presence of the particular type of bacteria of interest, as described herein.

In Northern analysis (see Current Protocols in Molecular Biology, Ausubel, F. et al., eds., John Wiley & Sons, supra), the hybridization methods described above are used to identify the presence of a sequence of interest in an RNA, such as unprocessed, partially processed or fully processed rRNA. For Northern analysis, a test sample comprising RNA is prepared from a biological sample from the subject by appropriate means. Specific hybridization of a nucleic acid probe, as described above, to RNA from the biological sample is indicative of the presence of the particular type of bacteria of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a particular bacterial nucleic acid sequence. Hybridization of the PNA probe to a nucleic acid sequence is indicative of the presence of the particular type of bacteria of interest.

Direct sequence analysis can also be used to detect a bacterial nucleic acid of interest. A sample comprising DNA or RNA can be used, and PCR or other appropriate methods can be used to amplify all or a fragment of the nucleic acid, and/or its flanking sequences, if desired. The bacterial nucleic acid, or a fragment thereof, is determined, using standard methods.

In another embodiment, arrays of oligonucleotide probes that are complementary to target microbial nucleic acid sequences can be used to detect and identify microbial nucleic acids. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and scanned for particular bacterial nucleic acids. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target bacterial nucleic acid sequence is amplified by well-known amplification techniques, e.g., PCR. Typically, this involves the use of primer sequences that are complementary to the target sequence. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Other methods of nucleic acid analysis can be used to detect microbial nucleic acids of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (1981, Sheffield et al., Proc. Natl. Acad. Sci. USA 86:232-236), mobility shift analysis (1989, Orita et al., Proc. Natl. Acad. Sci. USA 86:2766-2770; 1987, Rosenbaum and Reissner, Biophys. Chem. 265:1275; 1991, Keen et al., Trends Genet. 7:5); restriction enzyme analysis (1978, Flavell et al., Cell 15:25; 1981, Geever, et al., Proc. Natl. Acad. Sci. USA 78:5081); heteroduplex analysis; chemical mismatch cleavage (CMC) (1985, Cotton et al., Proc. Natl. Acad. Sci. USA 85:4397-4401); RNase protection assays (1985, Myers, et al., Science 230:1242); use of polypeptides which recognize nucleotide mismatches, such as *E. coli* mutS protein (see, for example, U.S. Pat. No. 5,459,039); Luminex xMAP™ technology; high-throughput sequencing (HTS) (2011, Gundry and Vijg, Mutat Res, doi:10.1016/j.mrfmmm.2011.10.001); next-generation sequencing (NGS) (2009, Voelkerding et al., Clinical Chemistry 55:641-658; 2011, Su et al., Expert Rev Mol Diagn. 11:333-343; 2011, Ji and Myllykangas, Biotechnol Genet Eng Rev 27:135-158); ion semiconductor sequencing (2011, Rusk, Nature Methods doi:10.1038/nmeth.f.330; 2011, Rothberg et al., Nature 475:348-352) and/or allele-specific PCR, for example. These and other methods can be used to identify the presence of one or more microbial nucleic acids of interest, in a biological sample derived from a subject. In various embodiments of the invention, the methods of assessing a biological sample for the presence or absence of a particular nucleic acid sequence, as described herein, are used to detect, identify or quantify particular constituents of a subject's microbiota, and to aid in the diagnosis of an altered microbiota associated with an inflammatory disease or disorder in a subject in need thereof.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}$P, $^{33}$P, $^{35}$S or $^{3}$H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. Nucleic acid herein refers to RNA, including mRNA, and DNA, including genomic DNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a fresh or fixed biological sample.

Routine methods also can be used to extract DNA from a biological sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

There are many methods known in the art for the detection of specific nucleic acid sequences and new methods are continually reported. A great majority of the known specific nucleic acid detection methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, preferably at least 15 nucleotides, more preferably at least 25 nucleotides, having a sequence complementary to a desired region of the target nucleic acid of interest is hybridized in a sample, subjected to depolymerizing conditions, and the sample is treated with an ATP/luciferase system, which will luminesce if the nucleic sequence is present. In quantitative Southern blotting, levels of the target nucleic acid can be determined.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. Most preferably the detection of the duplex is done using at least one primer directed to the target nucleic acid. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

The expression "specifically hybridizing in stringent conditions" refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. Preferably, the Tm for the amplification step is in the range of about 59° C. to about 72° C. Most preferably, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1997, eds Current Protocols in Molecular Biology).

In a preferred embodiment, the process for determining the quantitative and qualitative profile according to the present invention is characterized in that the amplifications are real-time amplifications performed using a labeled probe, preferably a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a target bacterial nucleic acid, and more particularly the primer includes 12 or more contiguous nucleotides substantially complementary to the sequence flanking the nucleic acid sequence of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence. In another aspect, the length of the primer can vary in length, preferably about 15 to 28 nucleotides in length (e.g., 16, 17, 18, 19, 20, 21, 22, 23, 24, 25, 26, or 27 nucleotides in length).

The present invention also pertains to kits useful in the methods of the invention. Such kits comprise components useful in any of the methods described herein, including for example, hybridization probes or primers (e.g., labeled probes or primers), reagents for detection of labeled molecules, means for amplification of nucleic acids, means for analyzing a nucleic acid sequence, and instructional materials. For example, in one embodiment, the kit comprises components useful for analysis of a bacterial nucleic acid of interest present in a biological sample obtained from a subject. In a preferred embodiment of the invention, the kit comprises components for detecting one or more of the bacterial nucleic acids of interest present in a biological sample derived from a subject.

Methods of Treatment

In some embodiments, the invention relates to methods of modifying an altered microbiota having secretory antibody-coated constituents in a subject in need thereof. In some embodiments, the invention provides compositions and methods for supplementing constituents of an altered microbiota that are under-represented in the altered microbiota, as compared with a normal microbiota, to restore the subject's microbiota to a normal microbiota. In other embodiments, the invention provides compositions and methods for diminishing constituents of an altered microbiota that are over-represented in the altered microbiota as compared with a normal microbiota, such as over-represented secretory antibody-coated constituents, to restore the subject's microbiota to a normal microbiota. As used throughout herein, constituents of an altered microbiota that are over-represented in the altered microbiota as compared with a normal microbiota, include constituents that are uniquely present in the altered microbiota as compared with a normal microbiota. In further embodiments, the invention provides compositions and methods for both supplementing constituents of an altered microbiota that are under-represented in the altered microbiota, as well as diminishing constituents of an altered microbiota that are over-represented in the altered microbiota, as compared with a normal microbiota, to restore the subject's microbiota to a normal microbiota. The microbiota of the subject can be any microbiota present on any mucosal surface of subject where antibody is secreted, including the gastrointestinal tract, the respiratory tract, genitourinary tract and mammary gland.

In conjunction with the diagnostic methods, the present invention also provides therapeutic methods for treating an inflammatory disease or disorder associated with an altered microbiota including secretory antibody-coated microbes, by modifying the microbiota to that observed in a healthy subject. In some embodiments, the methods supplement the numbers of the types of microbes that are under-represented in the altered microbiota. In other embodiments, the methods diminish the numbers of the types of microbes, including secretory antibody-coated microbes that are overrepresented in the altered microbiota. In a further embodiment, the methods both supplement the numbers of the types of bacteria that are under-represented in the altered microbiota, and diminish the numbers of the types of bacteria that are overrepresented in the altered microbiota. In various embodiments, the inflammatory diseases and disorders treatable by the methods of the invention include, but are not limited to: inflammatory bowel disease, celiac disease, colitis, intestinal hyperplasia, metabolic syndrome, obesity, rheumatoid arthritis, liver disease, hepatic steatosis, fatty liver disease, non-alcoholic fatty liver disease (NAFLD), or non-alcoholic steatohepatitis (NASH).

In some embodiments, modification of the altered microbiota is achieved by administering to a subject in need thereof a therapeutically effective amount of a probiotic composition comprising an effective amount of at least one type of bacteria, or a combinations of several types of bacteria, wherein the administered bacteria supplements the number of the types of bacteria which are under-represented in the altered microbiota, as compared with a normal microbiota.

Bacteria administered according to the methods of the present invention can comprise live bacteria. One or several different types of bacteria can be administered concurrently or sequentially. Such bacteria can be obtained from any source, including being isolated from a microbiota and grown in culture using known techniques.

In certain embodiments, the administered bacteria used in the methods of the invention further comprise a buffering agent. Examples of useful buffering agents include sodium bicarbonate, milk, yogurt, infant formula, and other dairy products.

Administration of a bacterium can be accomplished by any method suitable for introducing the organisms into the desired location. The bacteria can be mixed with a carrier and (for easier delivery to the digestive tract) applied to a liquid or to food. The carrier material should be non-toxic to the bacteria as wells as the subject. Preferably, the carrier contains an ingredient that promotes viability of the bacteria during storage. The formulation can include added ingredients to improve palatability, improve shelf-life, impart nutritional benefits, and the like.

The dosage of the administered bacteria will vary widely, depending upon the nature of the inflammatory disease or disorder, the character of subject's altered microbiota, the subject's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the gastrointestinal tract with the desired bacteria. In some embodiments, the dose ranges from about $10^6$ to about $10^{10}$ CFU per administration. In other embodiments, the dose ranges from about $10^4$ to about $10^6$ CFU per administration.

In certain embodiments, the present invention relates to a method for modifying an altered microbiota comprising administering to a subject in need of such treatment, an effective amount of at least one gastric, esophageal, or intestinal bacterium, or combinations thereof. In a preferred embodiment, the bacteria are administered orally. Alternatively, bacteria can be administered rectally or by enema.

The organisms contemplated for administration to modify the altered microbiota include any of the bacteria identified herein as under-represented in an altered microbiota. One of the organisms contemplated for administration to modify the altered microbiota is at least one *Lactobacillus* spp. In certain embodiments, the bacteria administered in the therapeutic methods of the invention comprise administration of a combination of organisms.

While it is possible to administer a bacteria for therapy as is, it may be preferable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the recipient thereof. Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

Although there are no physical limitations to delivery of the formulations of the present invention, oral delivery is preferred for delivery to the digestive tract because of its ease and convenience, and because oral formulations readily accommodate additional mixtures, such as milk, yogurt, and infant formula. For delivery to colon, bacteria can be also administered rectally or by enema.

In other embodiments, modification of the altered microbiota having over-represented secretory antibody-coated constituents is achieved by administering to a subject in need thereof a therapeutically effective amount of a vaccine to induce an immune response against the over-represented constituent, wherein the administered vaccine and ensuing immune response diminishes the number of at least one type of secretory antibody-coated bacteria that is over-represented in the altered microbiota, as compared with a normal microbiota. In various embodiments, the at least one type of bacteria that is diminished using the methods of the invention includes a Segmented Filamentous Bacteria (SFB) or *Helicobacter flexispira*, or a bacteria from at least one family selected from the group consisting of *Lactobacillus, Helicobacter*, S24-7, Erysipelotrichaceae and Prevotellaceae. In some embodiments, the bacteria from the family Prevotellaceae is a bacteria from the genera of *Paraprevotella* or *Prevotella*. In other embodiments, the secretory antibody-coated constituent of the subject's microbiota associated with the development or progression of an inflammatory disease or disorder in the subject is at least one selected from *Eubacterium, Eubacterium biforme, Eubacterium dolichum, Ruminococcus gnavus, Acidaminococcus, Actinomyces, Allobaculum, Anaerostipes, Bacteroides, Bacteroides fragilis, Bacteroides* Other, *Bifidobacterium, Bifidobacterium adolescentis, Bifidobacterium* Other, *Blautia, Blautia obeum, Blautia* Other, *Blautia producta, Bulleidia* Other, *Clostridium, Clostridium perfringens, Collinsella aerofaciens, Coprococcus, Coprococcus catus, Dialister, Eggerthella lenta*, Erysipelotrichaceae, *Faecalibacterium prausnitzii, Haemophilus parainfluenzae*, Lachnospiraceae, Lachnospiraceae other, *Lactobacillus, Lactobacillus mucosae, Lactobacillus* Other, *Lactobacillus reuteri, Lactobacillus zeae, Oscillospira, Pediococcus* Other, Rikenellaceae, *Roseburia, Roseburia faecis*, Ruminococcaceae, *Ruminococcus, Ruminococcus bromii*, SMB53, *Streptococcus, Streptococcus luteciae, Streptococcus* Other, *Sutterella, Turicibacter*, UC Clostridiales, UC Erysipelotrichaceae, UC Ruminococcaceae, *Veillonella, Veillonella dispar*, and *Weissella*.

In other embodiments, modification of the altered microbiota having over-represented secretory antibody-coated constituents is achieved by administering to a subject in need thereof a therapeutically effective amount of a passive immunotherapy or passive vaccine, such as by the administration of immunoglobulin (e.g., IgA) against the over-represented constituent, wherein the administered passive vaccine and ensuing immune response diminishes the number of at least one type of secretory antibody-coated bacteria that is over-represented in the altered microbiota, as compared with a normal microbiota. In some embodiments, the immunoglobulin is administered orally. Alternatively, the immunoglobulin can be administered rectally or by enema. In various embodiments, the at least one type of bacteria that is diminished using the methods of the invention includes a Segmented Filamentous Bacteria (SFB) or *Helicobacter flexispira*, or a bacteria from at least one family selected from the group consisting of *Lactobacillus, Helicobacter*, S24-7, Erysipelotrichaceae and Prevotellaceae. In some embodiments, the bacteria from the family Prevotellaceae is a bacteria from the genera of *Paraprevotella* or *Prevotella*. In other embodiments, the secretory antibody-coated constituent of the subject's microbiota associated with the development or progression of an inflammatory disease or disorder in the subject is at least one selected from *Eubacterium, Eubacterium biforme, Eubacterium dolichum, Ruminococcus gnavus, Acidaminococcus, Actinomyces, Allobaculum, Anaerostipes, Bacteroides, Bacteroides fragilis, Bacteroides* Other, *Bifidobacterium, Bifidobacterium adolescentis, Bifidobacterium* Other, *Blautia, Blautia obeum, Blautia* Other, *Blautia producta, Bulleidia* Other, *Clostridium, Clostridium perfringens, Collinsella aerofaciens, Coprococcus, Coprococcus catus, Dialister, Eggerthella lenta*, Erysipelotrichaceae, *Faecalibacterium prausnitzii, Haemophilus parainfluenzae*, Lachnospiraceae, Lachnospiraceae other, *Lactobacillus, Lactobacillus mucosae, Lactobacillus* Other, *Lactobacillus reuteri, Lactobacillus zeae, Oscillospira, Pediococcus* Other, Rikenellaceae, *Roseburia, Roseburia faecis*, Ruminococcaceae, *Ruminococcus, Ruminococcus bromii*, SMB53, *Streptococcus, Streptococcus luteciae, Streptococcus* Other, *Sutterella, Turicibacter*, UC Clostridiales, UC Erysipelotrichaceae, UC Ruminococcaceae, *Veillonella, Veillonella dispar*, and *Weissella*.

In other embodiments, modification of the altered microbiota having over-represented secretory antibody-coated constituents is achieved by administering to a subject in need thereof a therapeutically effective amount of antibiotic composition comprising an effective amount of at least one antibiotic, or a combinations of several types of antibiotics, wherein the administered antibiotic diminishes the number of at least one type of secretory antibody-coated bacteria that is over-represented in the altered microbiota, as compared with a normal microbiota. In various embodiments, the at least one type of bacteria that is diminished using the methods of the invention includes a Segmented Filamentous Bacteria (SFB) or *Helicobacter flexispira*, or a bacteria from at least one family selected from the group consisting of *Lactobacillus, Helicobacter*, S24-7, Erysipelotrichaceae and Prevotellaceae. In some embodiments, the bacteria from the family Prevotellaceae is a bacteria from the genera of *Paraprevotella* or *Prevotella*. In other embodiments, the secretory antibody-coated constituent of the subject's microbiota associated with the development or progression of an inflammatory disease or disorder in the subject is at least one selected from *Eubacterium, Eubacterium biforme, Eubacterium dolichum, Ruminococcus gnavus, Acidaminococcus, Actinomyces, Allobaculum, Anaerostipes, Bacteroides, Bacteroides fragilis, Bacteroides* Other, *Bifidobacterium, Bifidobacterium adolescentis, Bifidobacterium* Other, *Blautia, Blautia obeum, Blautia* Other, *Blautia producta, Bulleidia* Other, *Clostridium, Clostridium perfringens, Collinsella aerofaciens, Coprococcus, Coprococcus catus, Dialister, Eggerthella lenta*, Erysipelotrichaceae, *Faecalibacterium prausnitzii, Haemophilus parainfluenzae*, Lachnospiraceae, Lachnospiraceae other, *Lactobacillus, Lactobacillus mucosae, Lactobacillus* Other, *Lactobacillus reuteri, Lactobacillus zeae, Oscillospira, Pediococcus* Other, Rikenellaceae, *Roseburia, Roseburia faecis*, Ruminococcaceae, *Ruminococcus, Ruminococcus bromii*, SMB53, *Streptococcus, Streptococcus luteciae, Streptococcus* Other, *Sutterella, Turicibacter*, UC Clostridiales, UC Erysipelotrichaceae, UC Ruminococcaceae, *Veillonella, Veillonella dispar*, and *Weissella*.

The type and dosage of the administered antibiotic will vary widely, depending upon the nature of the inflammatory disease or disorder, the character of subject's altered microbiota, the subject's medical history, the frequency of administration, the manner of administration, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In various embodiments, the administered antibiotic is at least one of lipopeptide, fluoroquinolone, ketolide, cephalosporin, amikacin, gentamicin, kanamycin, neomycin, netilmicin, paromomycin, streptomycin, tobramycin, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime cefluprenam, cefoselis, cefozopran, cefpirome, cefquinome, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, ceftaroline, ceftioxide, cefuracetime, imipenem, primaxin, doripenem, meropenem, ertapenem, flumequine, nalidixic acid, oxolinic acid, piromidic acid pipemidic acid, rosoxacin, ciprofloxacin, enoxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, azithromycin, erythromycin, clarithromycin, dirithromycin, roxithromycin, telithromycin, amoxicillin, ampicillin, bacampicillin, carbenicillin, cloxacillin, dicloxacillin, flucloxacillin, mezlocillin, nafcillin, oxacillin, penicillin g, penicillin v, piperacillin, pivampicillin, pivmecillinam, ticarcillin, sulfamethizole, sulfamethoxazole, sulfisoxazole, trimethoprim-sulfamethoxazole, demeclocycline, doxycycline, minocycline, oxytetracycline, tetracycline, linezolid, clindamycin, metronidazole, vancomycin, vancocin, mycobutin, rifampin, nitrofurantoin, chloramphenicol, or derivatives thereof.

In a further embodiment, modification of the altered microbiota is achieved by both administering at least one type of bacteria to supplement the numbers of at least one type of bacteria that is under-represented in the altered microbiota, and administering at least one antibiotic to diminish the numbers of at least one type of bacteria that is over-represented in the altered microbiota.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: IgA Coating of the Intestinal Microbiota in Health and Disease

Immunoglobulin A represents one of the major mechanisms by which the adaptive immune system controls commensal bacteria in the gastrointestinal tract. However, little is known about the specificity of the intestinal IgA response. To better understand interactions between the immune system and the microbiota and to identify intestinal bacteria that preferentially stimulate immune responses, IgA coating of the intestinal microbiota was examined by separating IgA-coated and non-coated bacteria and performing 16S rRNA sequencing. While it was found that each individual displays a unique set of IgA coated bacterial species, IgA coating of select bacterial taxa was conserved within the healthy human population. Notably, inflammatory bowel disease (IBD) patients and mice with a colitogenic dysbiosis displayed dramatically altered patterns of IgA coating, suggesting dysregulation of host-microbiota homeostasis, and showed high coating of bacterial species that were uniquely present in dysbiosis or in patients with IBD. Given the importance of IgA in maintenance of host-microbiota symbiosis, highly IgA-coated taxa appear to play novel and critical roles in shaping the immune response and host physiology in health and disease.

Described herein is a novel technique named IgA-SEQ that combines flow cytometry-based bacterial cell sorting and 16S ribosomal RNA-based metagenomic analyses to sort and identify IgA-coated bacterial species from the intestinal microbiota. Because many disease-causing members of the microbiota may cause disease because they trigger the immune response, including IgA production and secretion, IgA-SEQ can accurately identify bacteria that are responsible for driving disease development in populations or in a particular individual. Therefore, in the methods described herein, the immune response is utilized to identify putative disease-causing bacteria by determining which bacterial species are targeted by an individual host's immune system. The methods described herein exploit the host's immune response to the microbiota to identify disease-causing bacteria in the intestine in an individualized manner. Although the methods described herein are useful at the individual level, patterns and trends identified in multiple individuals can be used to identify characteristics of populations of individuals. IgA-SEQ was shown to accurately identify disease-causing members of the microbiota in mice with a microbiota that exacerbates colitis. This technique is also useful to identify disease-causing bacteria in patients with a variety of other inflammatory diseases and disorders, including, by way of non-limiting example, Crohn's disease.

The materials and methods employed in these experiments are now described.

Animals

ASC-deficient mice were bred and maintained at the Yale University School of Medicine and all treatments were in accordance with Yale Animal Care and Use Committee guidelines. Wild type mice were from the National Cancer Institute (NCI; Charles River).

Inflammasome-Mediated Intestinal Dysbiosis

Intestinal dysbiosis was induced by co-housing wild type C57Bl/6 mice from NCI with ASC-deficient mice at a 1 to 1 ratio for at least 6 weeks.

DSS Colitis

SPF and SPF$^{dysbiosis}$ mice were treated with 2% Dextran Sodium Sulfate (MP Biomedicals) in the drinking water ad libitum for 7 days to induce colitis. Weight was measured each day for 14 days.

ELISA

Pre-sort, IgA+ and IgA− fractions (after MACS sorting) were probed for IgA by ELISA (Coating: MP Biomedicals 55478, Detection: Sigma B2766).

Fecal IgA Flow Cytometry

Fecal pellets from mice or ~100 mg of human fecal material were collected in Fast Prep Lysing Matrix D tubes containing ceramic beads (MP Biomedicals) and incubated in 1 mL Phosphate Buffered Saline (PBS) per 100 mg fecal material on ice for 1 hour. Fecal pellets were homogenized by bead beating for 5 seconds (Minibeadbeater; Biospec) and centrifuged (50×g, 15 min, 4° C.) to remove large particles. Fecal bacteria in the supernatants were removed (100 µl/sample), washed with 1 mL PBS containing 1% (w/v) Bovine Serum Albumin (BSA, American Bioanalytical; staining buffer) and centrifuged for 5 min (8,000×g, 4° C.) before resuspension in 1 mL staining buffer. A small sample of this bacterial suspension (20 µl) was saved as the Pre-sort sample for 16S sequencing analysis. After an additional wash, bacterial pellets were resuspended in 100 µl blocking buffer (staining buffer containing 20% Normal Rat Serum for mouse samples or 20% Normal Mouse Serum for human samples, both from Jackson ImmunoResearch), incubated for 20 min on ice, and then stained with 100 µl staining buffer containing PE-conjugated Anti-Mouse IgA (1:12.5; eBioscience clone mA-6E1) or PE-conjugated Anti-Human IgA (1:10; Miltenyi Biotec clone IS11-8E10) for 30 minutes on ice. Samples were then washed 3 times with 1 mL staining buffer before flow cytometric analysis or cell separation.

Sorting of IgA+ and IgA− Bacteria from Feces

Anti-IgA stained fecal bacteria were incubated in 1 ml staining buffer containing 50 µl Anti-PE Magnetic Activated Cell Sorting (MACS) beads (Miltenyi Biotec) (15 min at 4° C.), washed twice with 1 ml Staining Buffer (10,000×g, 5 min, 4° C.), and then sorted by MACS (Possel s program on an AutoMACS pro; Miltenyi). After MACS separation, 50 µl of the negative fraction was collected for 16S sequencing analysis (IgA-negative fraction). The positive fraction was then further purified via Fluorescence Activated Cell Sorting (FACSAria; BD Biosciences). For each sample, 2 million IgA-positive bacteria were collected, pelleted (10,000×g, 5 min, 4° C.), and frozen along with the Pre-sort and IgA-negative samples at −80° C. until 16S sequencing analysis.

Bacterial DNA Purification and 16S V4 PCR Amplification

All bacterial samples were suspended in 400 µl staining buffer before adding 250 µl 0.1 mm zirconia/silica beads (Biospec), 300 µl Lysis buffer (200 mM NaCl, 200 mM Tris, 20 mM EDTA, pH 8), 200 µl 20% SDS and 500 µl phenol:chloroform:isoamylalcohol (25:24:1, pH 7.9; Sigma). Samples were chilled on ice for 4 min and homogenized by beat beating (2 min bead beating, 2 min on ice, 2 min bead beating). After centrifugation (8000 rpm, 4° C.), the aqueous phase was transferred to a Phase Lock Gel tube (Light; 5 PRIME), an equal volume of phenol:chloroform:isoamylalcohol was added, samples were mixed by inversion and centrifuged for 3 min (13,200 rpm, room temperature). The DNA was then precipitated by adding 1/10 volume of 3M NaOAc (pH5.5) and 1 volume Isopropanol to the aqueous phase, followed by incubation at −20° C. overnight. Precipitated DNA was pelleted (20 min, 13,200 rpm, 4° C.), washed with 500 µl 100% EtOH (3 min, 13,200 rpm, 4° C.), dried (miVac GeneVac 15 min, no heat, Auto Run setting), resuspended in 100 µl of TE buffer (pH 7) and incubated at 50° C. for 30 min. The DNA was then treated with 35 U/ml RNase A (Qiagen) before purification (QIAquick PCR purification; Qiagen) and elution in 40 µl Elution Buffer. The V4 region of 16S ribosomal RNA was PCR amplified (28 cycles) in triplicate from purified DNA (10 µl per reaction) using Phusion polymerase (New England Bioscience) and the primer pair F515/R806. After amplification, PCR triplicates were pooled, purified using a MinElute kit (Qiagen), and resuspended in 20 µl $H_2O$. PCR products were then quantified via fluorimetry using Picogreen (Invitrogen) and pooled at a final concentration of 10 nM before sequencing using a miSeq sequencer (Illumina, 2×250 bp paired-end reads, up to 200 samples per sequencing run).

16S and Statistical Analysis

Paired end reads were assembled with a novel pipeline that uses PANDA-seq (Masella et al., 2012, BMC bioinformatics 13:31) and assigns consensus Q scores to the assembled reads. Microbial diversity was analyzed using the Quantitative Insights Into Microbial Ecology (QIIME version 1.7) analysis suite. Reads were demultiplexed and quality filtered (Q-score cutoff 30), then clustered into 97% identity Operational Taxonomic Units (OTUs) using the open-reference OTU picking workflow in QIIME and the Greengenes reference OTU database. Taxonomy was assigned to representative OTUs using the Ribosomal Database Project classifier (RDP) and the May 2013 Greengenes taxonomy (Caporaso et al., 2010, Nature methods 7:335; Wang et al., 2007, Applied and environmental microbiology 73:5261; Lozupone et al., 2005, Applied and environmental microbiology 71:8228). OTUs of less than 0.01% relative abundance and contaminating OTUs that were also found after sequencing of 16S amplicons from PCR samples without template DNA, were filtered from OTU tables. Filtered OTU tables were rarefied to a depth of 5000 sequences per sample for all further analyses.

All microbial ecology analyses (beta diversity, PCoA, PERMANOVA/adonis) were performed using QIIME and the Vegan package for R (version 2.1-21). Linear Discriminant Analysis Effect Size (LEfSe) analyses were performed using the LEfSe Galaxy module (huttenhower.sph.harvard.edu/galaxy). Wilcoxon rank-sum tests were performed using R. Taxa that were undetectable in both the IgA+ and IgA− fractions in a given sample were considered not present and were assigned as missing-values for Wilcoxon rank-sum tests. As LEfSe cannot handle missing values, these missing-values were replaced with zeros for all LEfSe analyses. To allow for the calculation of ICI scores for taxa that were undetectable in the IgA− fraction but detected in the IgA+ fraction, and which are therefore highly-coated, zeroes in the negative fraction were replaced with a relative abundance of 0.0002, which is the limit of detection (1 sequence in 5000).

Human Fecal Samples

The human study protocol was approved by the Institutional Review Board (Protocol No. 10-1047) of the Icahn Medical School at Mount Sinai, N.Y. The healthy subjects were recruited through the Mount Sinai Biobank or an advertisement. Fresh fecal samples were collected at home, stored at −20° C. in an insulated foam shipper, mailed to Mount Sinai overnight and then stored at −80° C. for further analysis. A short questionnaire was also administrated to collect participants' health information.

The results of the experiments are now described.

IgA-SEQ Analysis

Figure 1:
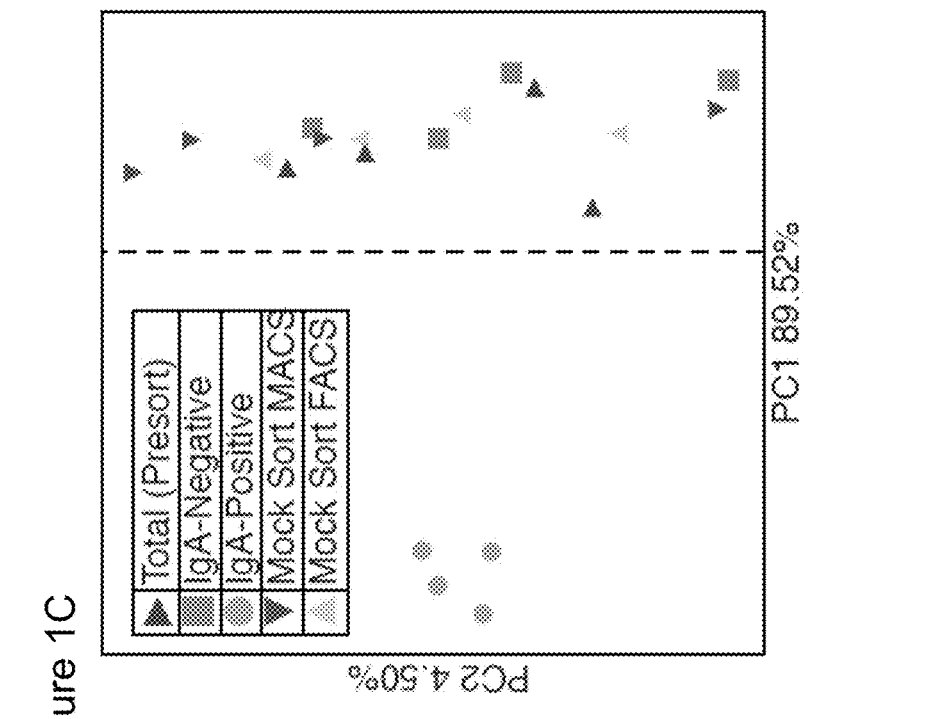
FIG. 1, comprising
Figure 1:
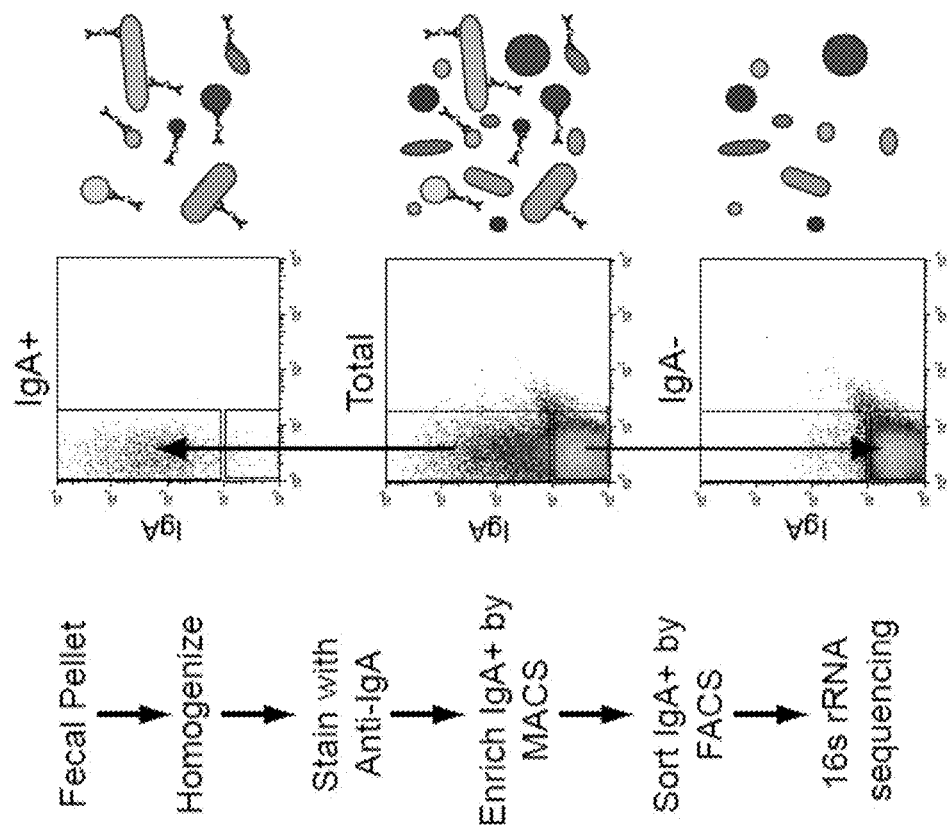
Figure 4:
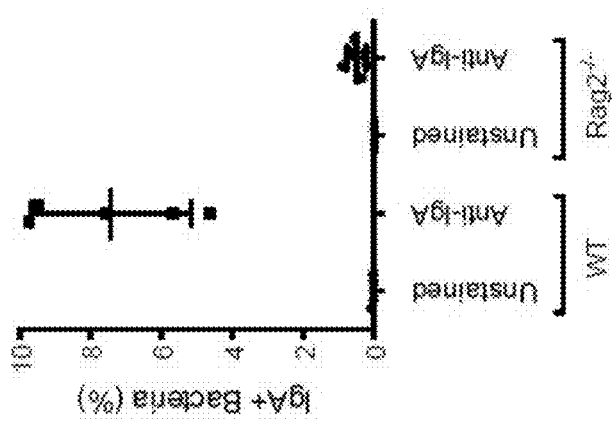
FIG. 4, comprising
Figure 4:
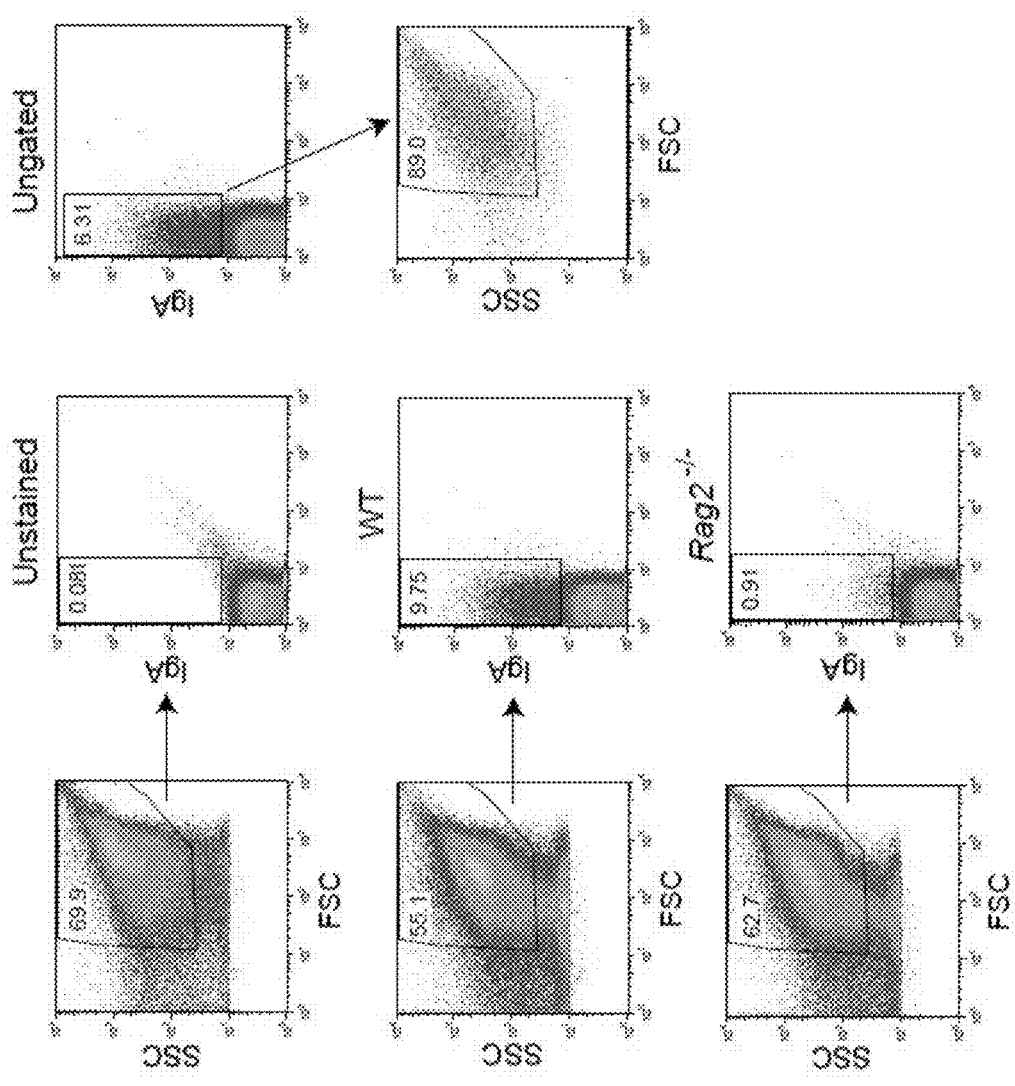
Figure 5:
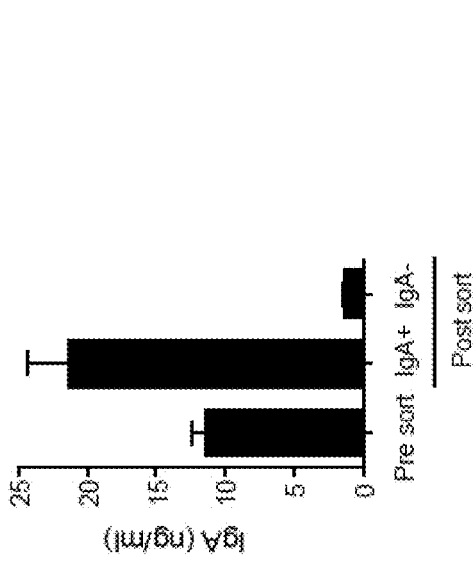
FIG. 5, comprising
Figure 5:
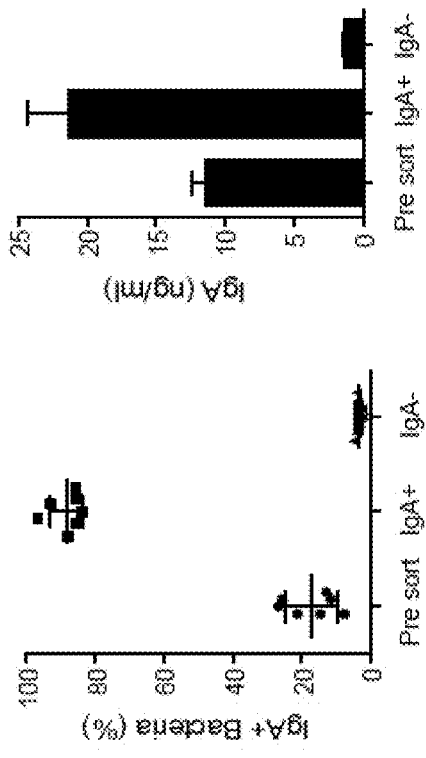
Figure 5:
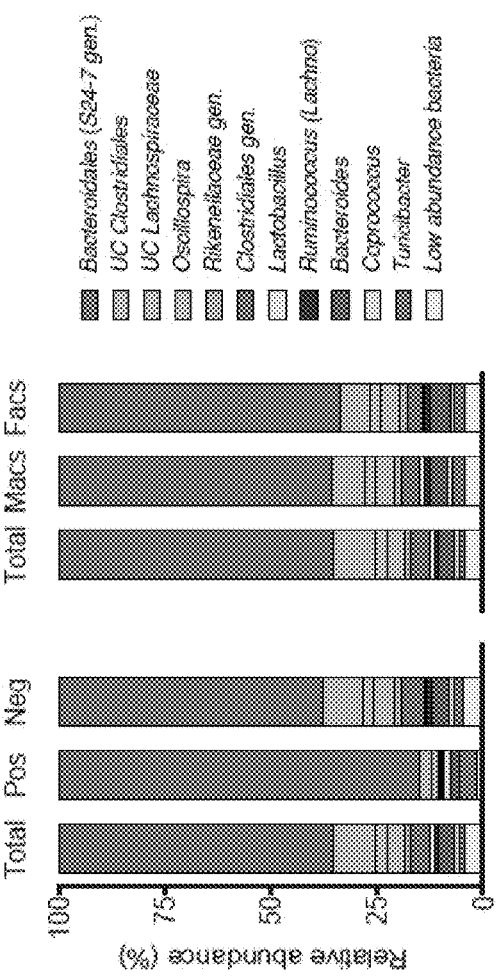

The studies described herein examine IgA coating of the intestinal microbiota in a comprehensive and unbiased manner in order to characterize patterns of IgA coating and determine if there are members of the microbiota that are preferentially recognized and targeted by the mucosal immune system. Therefore, an approach was devised combining antibody-based bacterial cell sorting and 16S ribosomal RNA gene sequencing to specifically isolate and identify IgA coated bacteria from fecal material (IgA-SEQ, FIG. 1A). First, staining of fecal bacteria from Specific Pathogen Free (SPF) mice for IgA confirmed that only a fraction of intestinal bacteria are measurably IgA coated, as determined by flow cytometry (FIGS. 4A and 4B); importantly, intestinal bacteria from recombination activating gene 2 (Rag2)-deficient mice, which cannot produce antibodies, showed negligible staining for IgA. IgA coated (IgA+) and non-coated (IgA−) bacteria were subsequently isolated using a combination of magnetic activated cell sorting (MACS) and fluorescence activated cell sorting (FACS) and confirmed the specificity and efficacy of the sorting by reanalyzing sorted fractions via flow cytometry (FIG. 1B; and FIG. 5A) and ELISA (FIG. 5B). Principal Coordinates Analysis (PCoA) and PERMANOVA analysis of weighted UniFrac distances of 16S rRNA sequences of total, IgA+ and IgA− fecal bacteria revealed that, instead of comprising a random sampling of all intestinal bacteria, IgA coated bacteria represent a phylogenetically distinct sub-community of the microbiota, as compared to total fecal bacteria or non-coated bacteria (P<0.05) (FIG. 1C and FIG. 5C). In contrast, total fecal bacteria and non-coated bacteria were not significantly different. Importantly, sorting by itself did not appreciably alter the observed microbial composition since PCoA and PERMANOVA analysis of weighted UniFrac distances showed no significant differences between mock sorted samples and the total microbiota (FIG. 1C and FIG. 5C). These data demonstrate that IgA coating of the microbiota is selective across microbial taxa, and show that IgA-coated bacteria represent a taxonomically distinct subset of intestinal bacteria in SPF mice.

Figure 2:
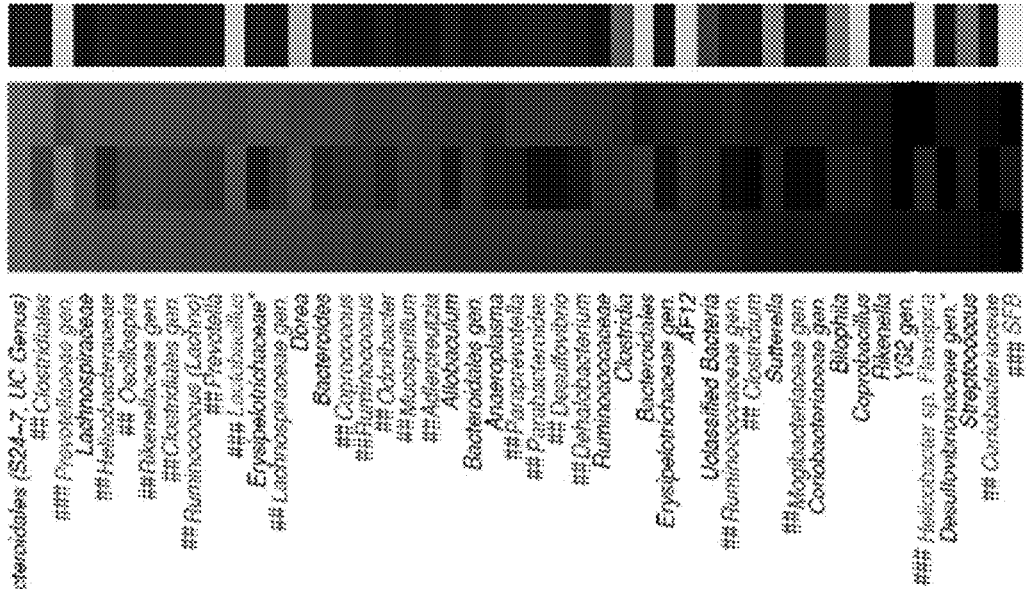
FIG. 2, comprising
Figure 2:
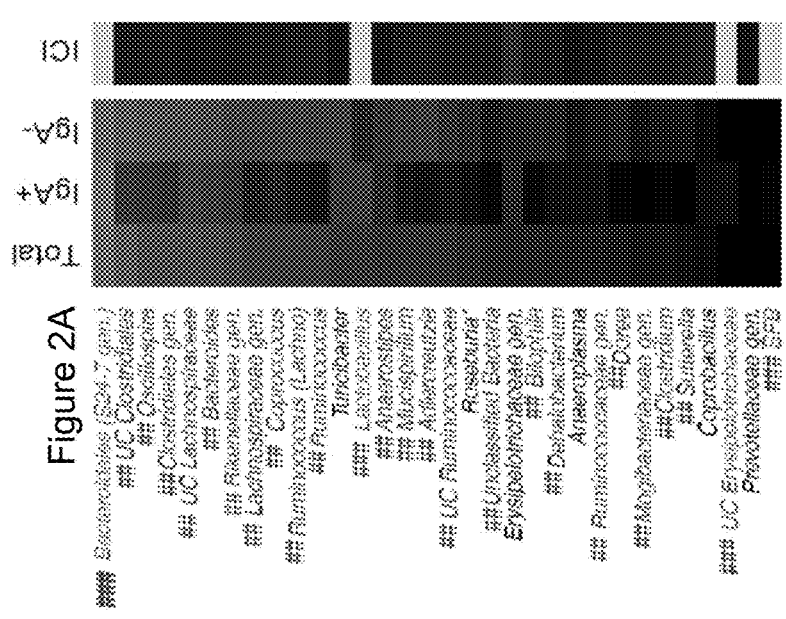
Figure 6:
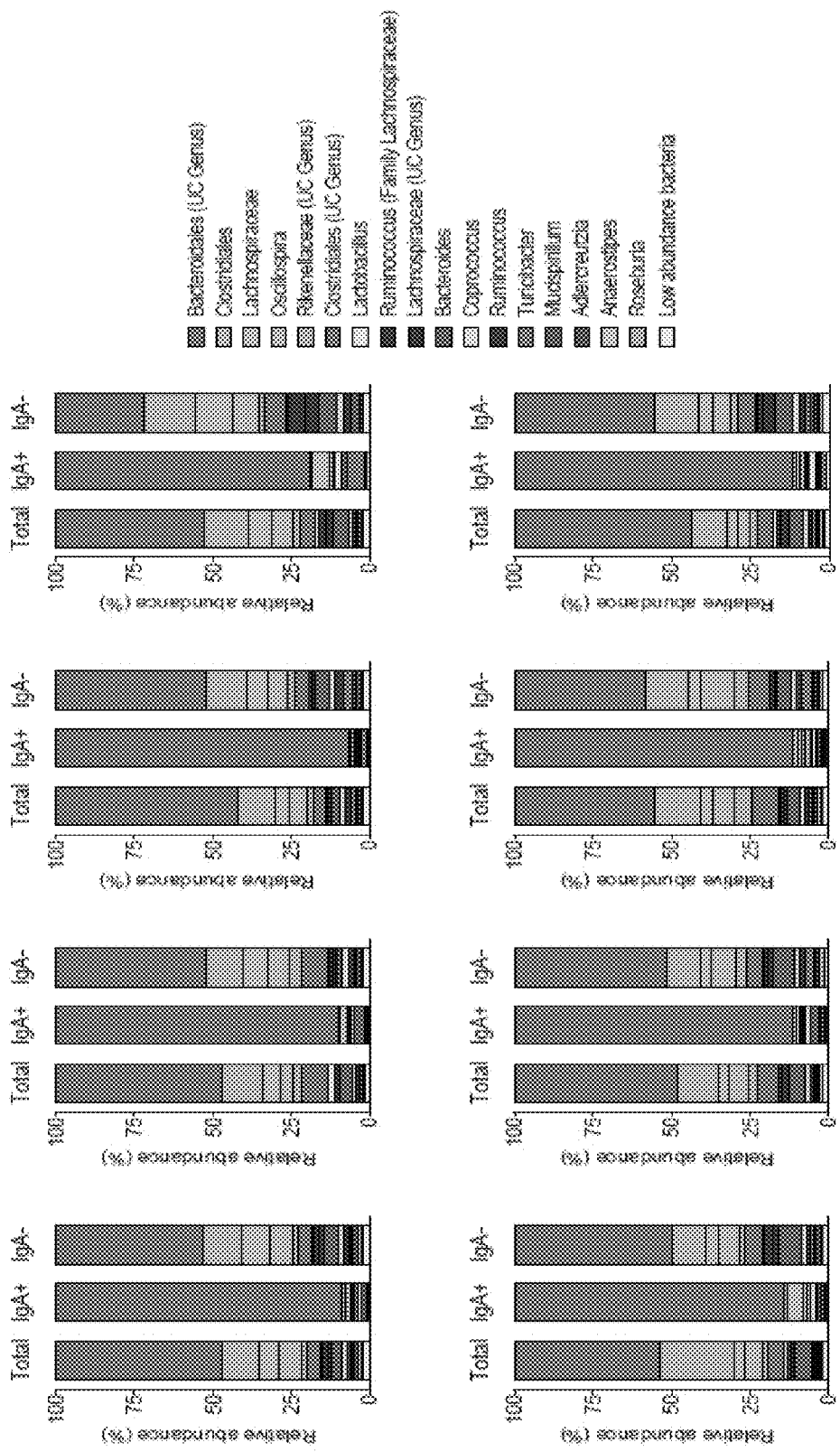
FIG. 6, comprising

To identify which specific bacterial taxa were highly coated with IgA, relative abundances of bacterial genera were examined in total, IgA coated bacteria and non-coated bacteria isolated from the feces of SPF mice (FIG. 2A; and FIG. 6). To quantify and compare relative levels of IgA coating between taxa, an IgA Coating Index (ICI) was calculated for each individual bacterial taxon as follows: $ICI=IgA+^{relative\ abundance}/IgA-^{relative\ abundance}$. Taxonomic abundance in the IgA+ and IgA− fractions were then compared using both the Wilcoxon rank-sum test and Linear Discriminant Analysis Effect Size (LEfSe; Segata et al., 2011, Genome biology 12:R60), which combines the Kruskal-Wallis sum-rank test, Wilcoxon rank-sum test and Linear Discriminant Analysis, to determine which taxa were enriched in either the IgA+ or IgA− fractions (FIG. 6B). Taxa that were significantly higher in the IgA+ fraction were classified as highly coated, whereas taxa that were significantly higher in the IgA− fraction were classified as low or non-coated. These analyses revealed that four genera were highly coated with IgA in SPF mice (P<0.05, LEfSe and Wilcoxon rank-sum): an unclassified genus of the family S24-7 from the order Bacteroidales, *Lactobacillus*, Segmented Filamentous Bacteria (SFB), and unclassified Erysipelotrichaceae. In addition, 22 taxa showed low or no coating with IgA (P<0.05, LEfSe and Wilcoxon rank-sum), while the remaining taxa were neither enriched nor depleted by IgA-based separation. These data demonstrate that only a small number of bacterial taxa are highly coated with IgA in mice with a complex microbiota.

The inflammasome is a critical component of the innate immune system that orchestrates the activation of Caspase-1 and release of the inflammatory cytokines IL-1β and IL-18 in response to infection (Strowig et al. 2012, Nature 481: 278). It was recently shown that mice lacking components of the inflammasome, such as the signaling adaptor apoptosis-associated speck-like protein containing a CARD (ASC), harbor a dysbiotic intestinal microbiota that can be transmitted to wild type SPF mice through co-housing (Elinav et al., 2011, Cell 145:745). This inflammasome-mediated dysbiosis is characterized by the expansion of Prevotellaceae species, which leads to an increase in the severity of chemically-induced colitis. To identify bacteria that are highly coated with IgA in the context of a colitogenic microbiota, IgA-SEQ was performed on SPF mice that had acquired inflammasome-mediated dysbiosis through co-housing with $Asc^{-/-}$ mice ($SPF^{dysbiosis}$). As previously reported, co-housing altered the composition of the intestinal microbiota and increased susceptibility to colitis (FIG. 7A to 7C). Flow cytometric analysis of IgA coating of the intestinal microbiota of $SPF^{dysbiosis}$ mice revealed an increase in the total percentage of intestinal bacteria coated with IgA as compared to SPF mice, suggesting that acquisition of dysbiosis may alter the pattern or extent of IgA coating (FIG. 7D). This was confirmed by PCoA and PERMANOVA analysis of weighted UniFrac distances of total, IgA+ and IgA− fractions, which showed that IgA coated bacteria in $SPF^{dysbiosis}$ mice are phylogenetically distinct from non-coated bacteria and from IgA coated bacteria in healthy SPF mice (FIG. 8A; P<0.05, PERMANOVA).

Figure 8:
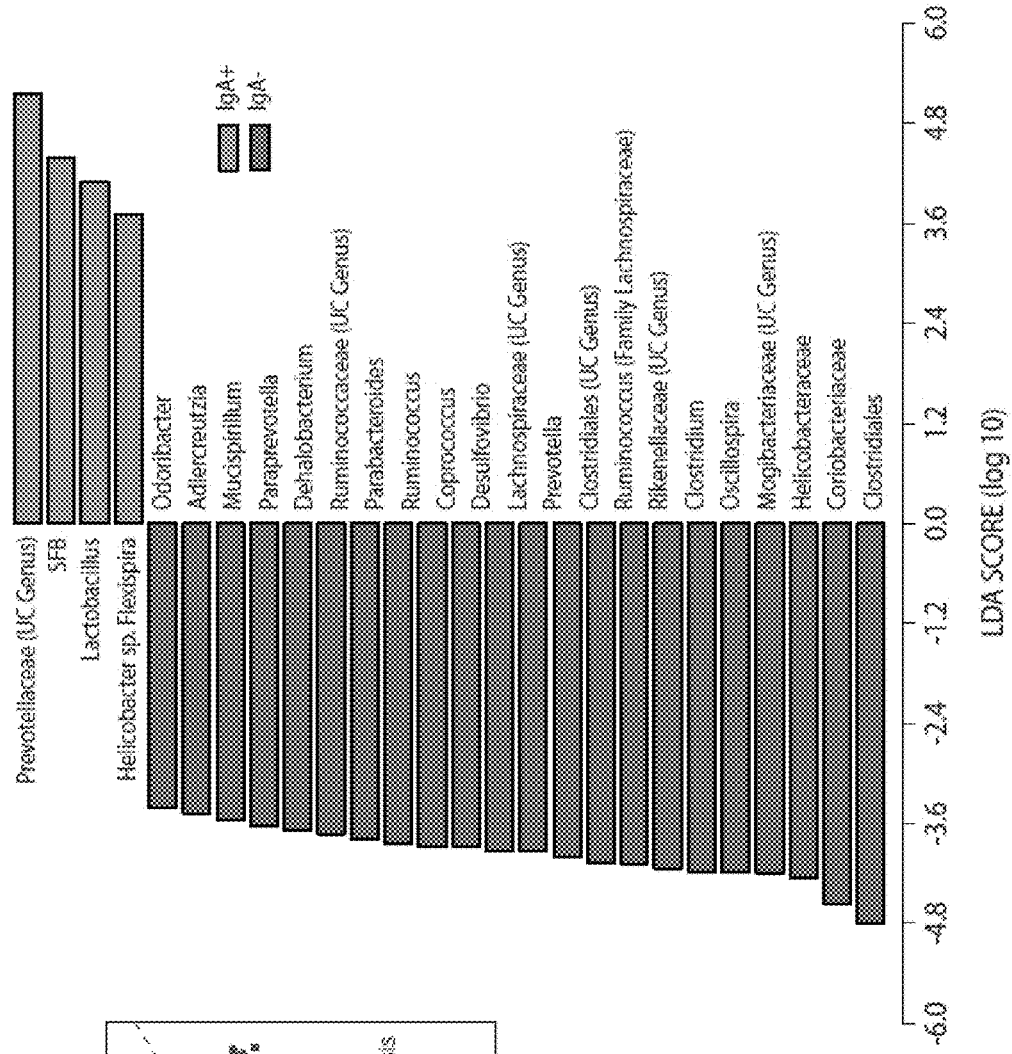
FIG. 8, comprising
Figure 8:
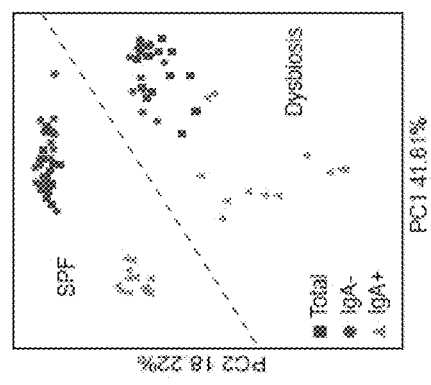
Figure 8:
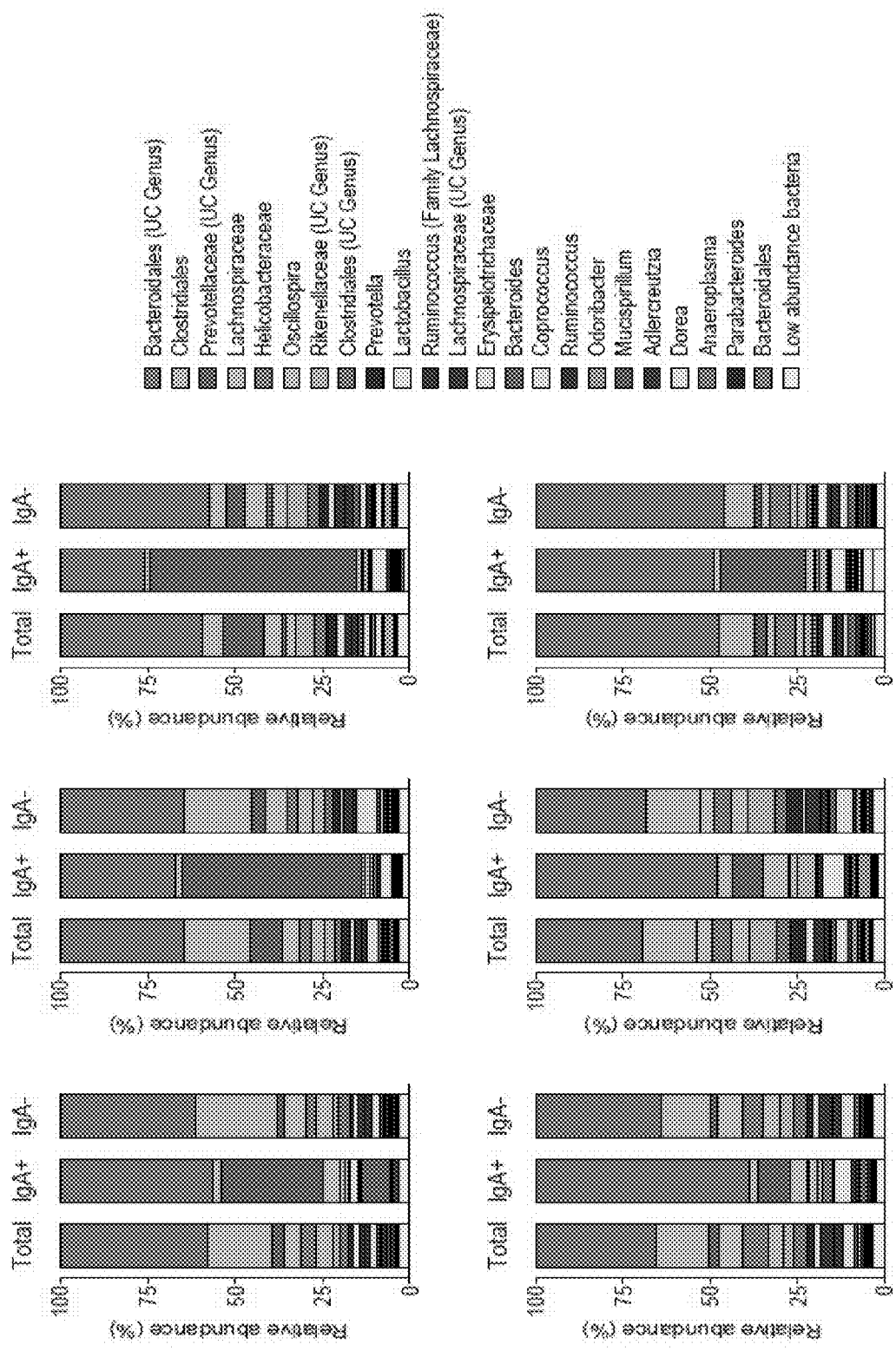

While 19 taxa in $SPF^{dysbiosis}$ mice showed significant expansion as a result of co-housing, only two of these taxa were highly coated with IgA (FIG. 2B, and FIGS. 8B and 8C; P<0.05 LEfSe and Wilcoxon rank-sum); the most abundant IgA coated taxon was an unclassified genus from the Prevotellaceae family, which is the defining taxon in inflammasome-mediated dysbiosis (Elinav et al., 2011, Cell 145: 745). *Helicobacter* sp. *flexispira*, which was acquired during co-housing, was also significantly enriched in the IgA coated fraction in $SPF^{dysbiosis}$ mice. Finally, as in SPF mice, *Lactobacillus* and SFB remain significantly enriched in the IgA coated fraction in mice with intestinal dysbiosis.

Figure 9:
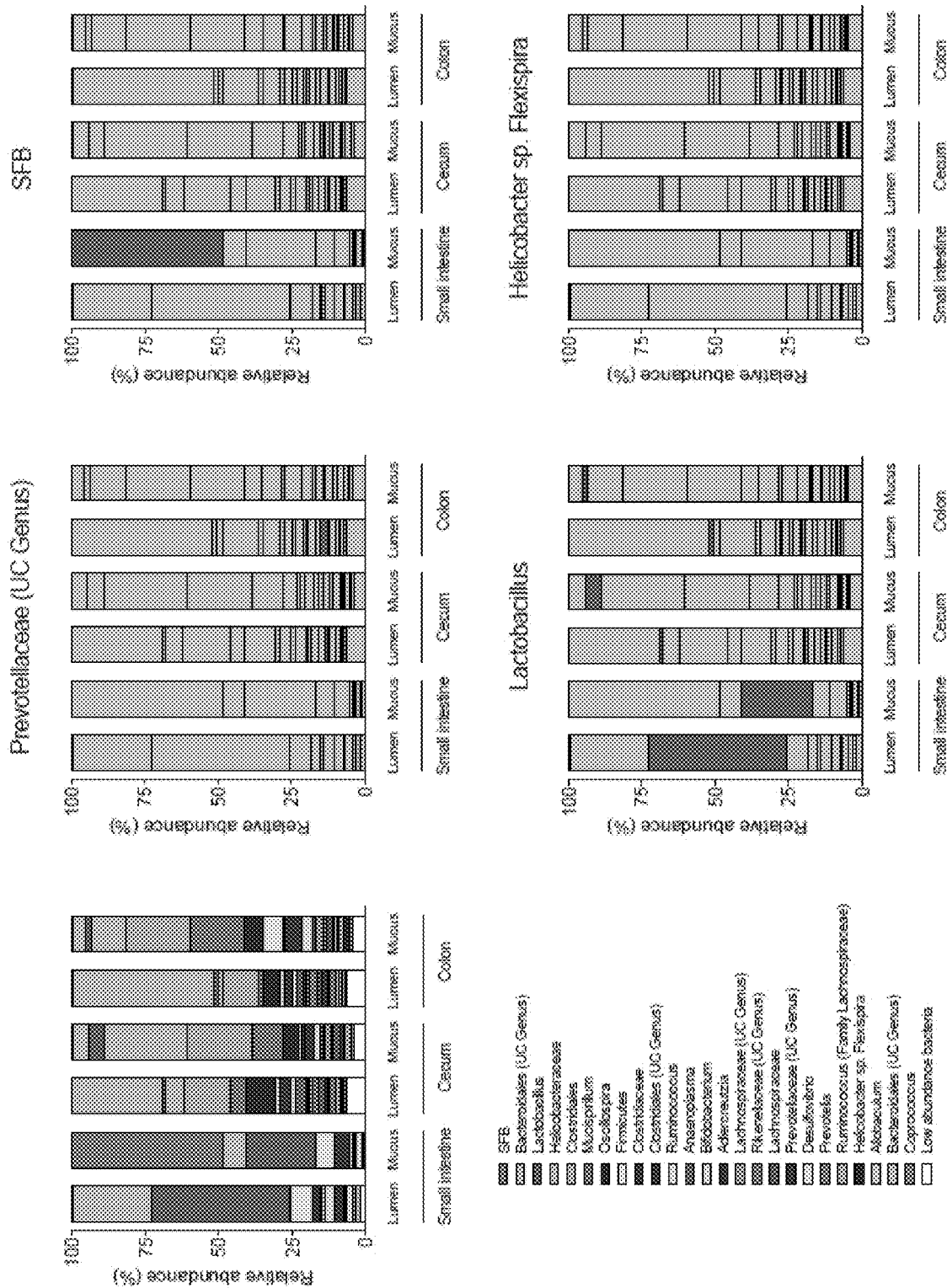
FIG. 9 depicts the results of experiments assessing IgA coating of luminal and mucus-associated bacteria from the small intestine, cecum and colon of SPF$^{dysbiosis}$ mice. Relative abundances of luminal and mucus-associated bacteria from the small intestine, cecum and colon of SPF$^{dysbiosis}$ mice (n=5).

Taken together, only six bacterial taxa were found to be highly coated with IgA in SPF or $SPF^{dysbiosis}$ mice: an unclassified genus of S24-7 from the order Bacteroidales, *Lactobacillus*, SFB, unclassified Erysipelotrichaceae, *Helicobacter* sp. *flexispira*, and an unclassified Prevotellaceae. This implies that the immune responses that were detected using IgA-SEQ are specific to bacterial antigens that are unique to particular members of the microbiota, rather than shared across bacterial taxa. The induction of such responses requires intimate interaction between the mucosal immune system and target bacteria. Indeed, IgA has been specifically implicated in controlling members of the microbiota that penetrate the mucus layer and attach to the intestinal epithelium, including SFB (Suzuki et al., 2004, 101:1981); such bacteria are natural targets for the mucosal immune response as their location close to the epithelium signals a potential threat and enables efficient sampling by cells of the intestinal immune system. To explore the possibility that IgA coated bacteria are mucus-associated, mucus-associated and luminal bacteria were isolated from the small intestine, cecum and colon of $SPF^{dysbiosis}$ mice and the distribution of IgA coated bacteria in these fractions was analyzed (FIG. 9). Small intestinal, cecal and large intestinal bacteria (e.g., SFB, Prevotellaceae, and *Helicobacter* sp. *flexispira*, respectively) were highly coated, suggesting that IgA coating does not strictly correlate with anatomical location. As predicted, multiple highly coated bacteria were indeed found in the mucus, including SFB and *Helicobacter* sp. *flexispira*, which were almost exclusively mucus-associated. However, mucus association alone was insufficient to trigger high IgA coating since many mucus-associated taxa were devoid of significant IgA coating (e.g., unclassified Helicobacteraceae, *Mucispirillum*, unclassified Clostridiales, and *Ruminococcus*) (FIG. 2B).

As the initiation of a bacterial-specific IgA response requires intimate interaction with the mucosal immune system, the taxa that were identified as highly coated may have broad effects on the intestinal immune system and, therefore, disease susceptibility. Indeed, four of the six taxa that were identified by IgA-SEQ are well characterized as members of the microbiota that modulate the intestinal immune response and thereby alter susceptibility to disease: SFB, *Lactobacillus*, Prevotellaceae, and *Helicobacter* (Hooper et al., 2012, Science 336:1268; Ivanov et al., 2009, Cell 139:485; Elinav et al., 2011, Cell 145:745). Additional investigation into the effects of the remaining IgA coated taxa (S24-7 and Erysipelotrichaceae) on the immune system is ongoing, although Erysipelotrichaceae species have been linked to obesity (Zhang et al., 2009, Proceedings of the National Academy of Sciences 106:2365).

Figure 10:
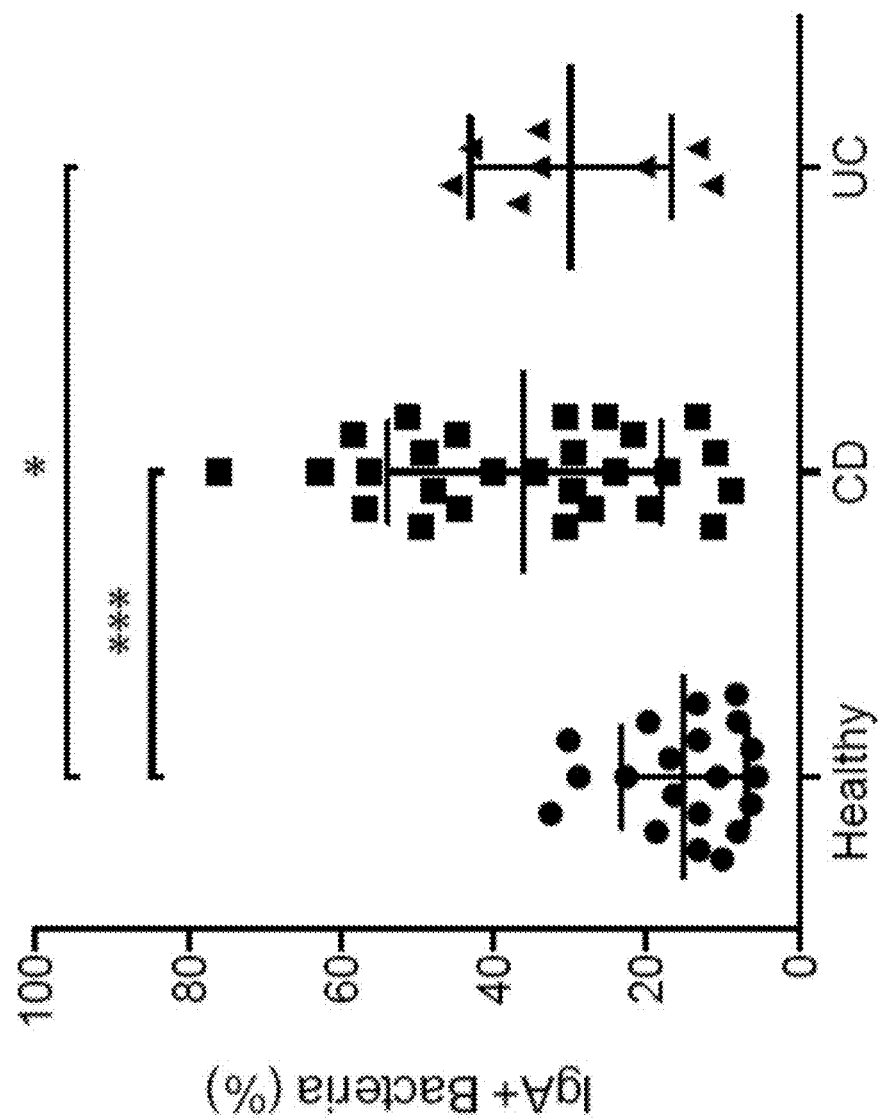
FIG. 10 depicts the results of experiments assessing IgA coating of fecal bacteria from healthy, Crohn's disease and Ulcerative colitis patients. IgA coating of fecal bacteria from 20 healthy subjects, 27 Crohn's disease patients (CD) and 8 Ulcerative colitis patients (UC) as measured by flow cytometry. *P<0.05, ***P<0.001 (one-way ANOVA).
Figure 11:
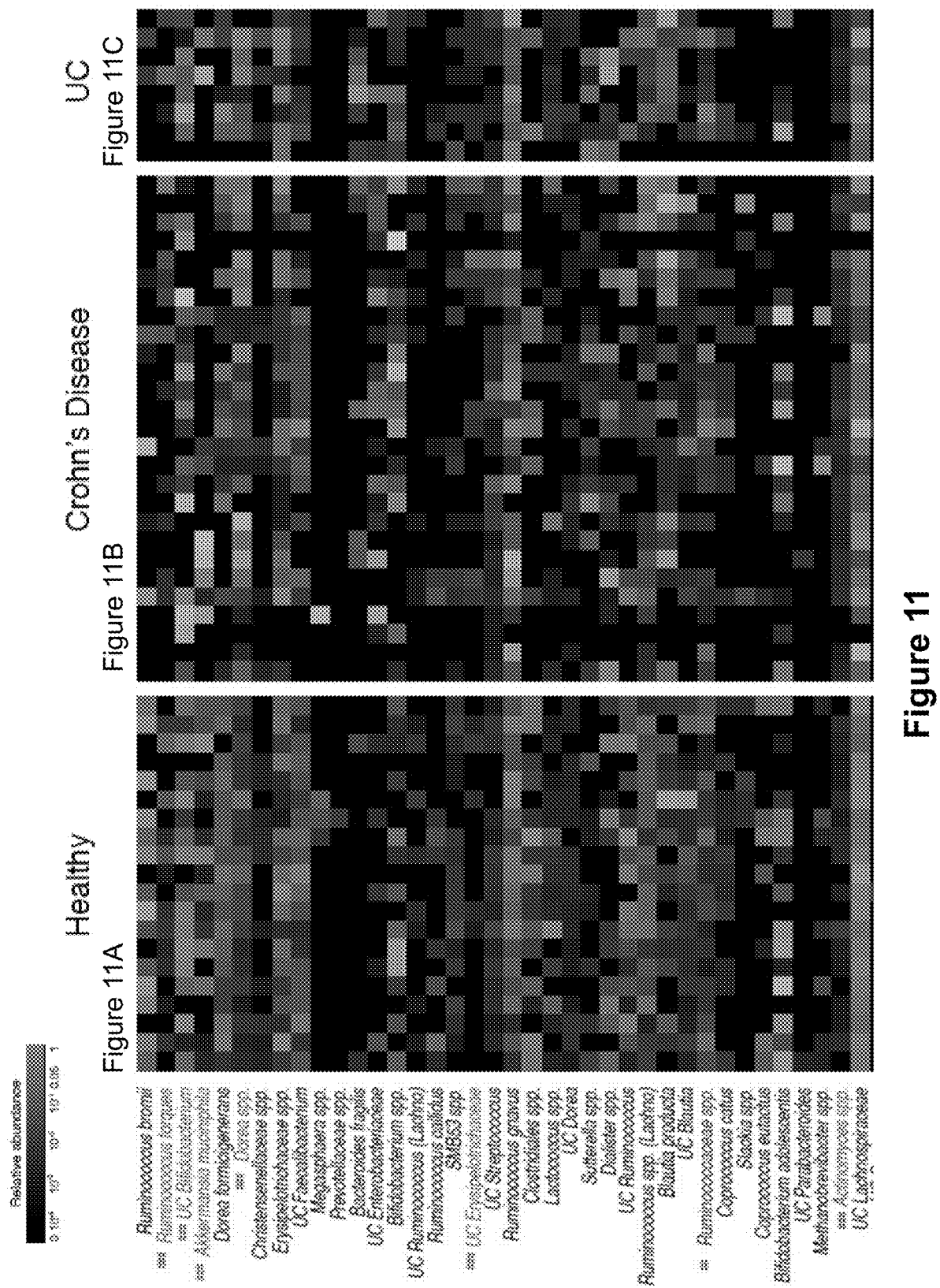
FIG. 11, comprising
Figure 11:
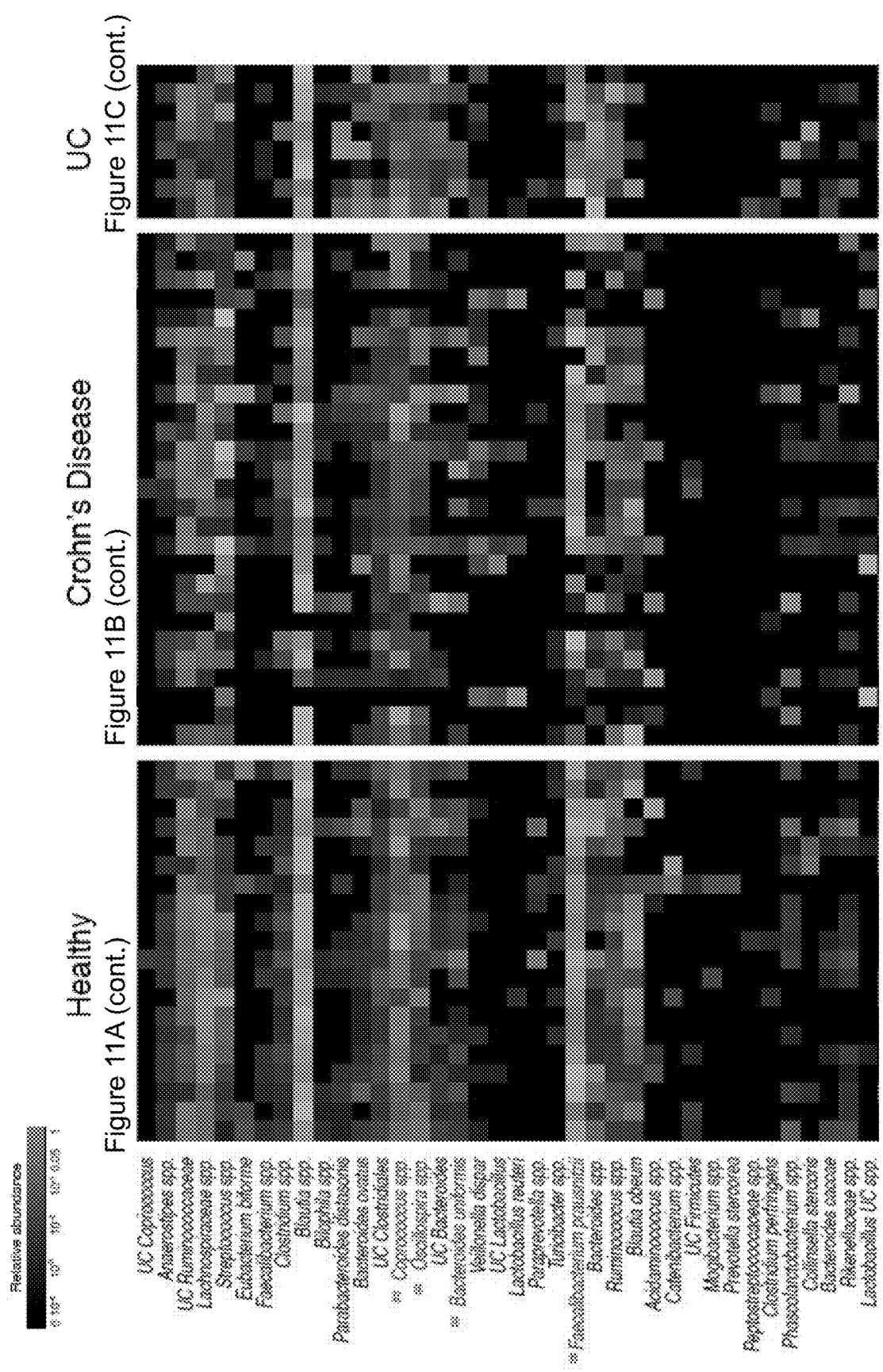
Figure 11:
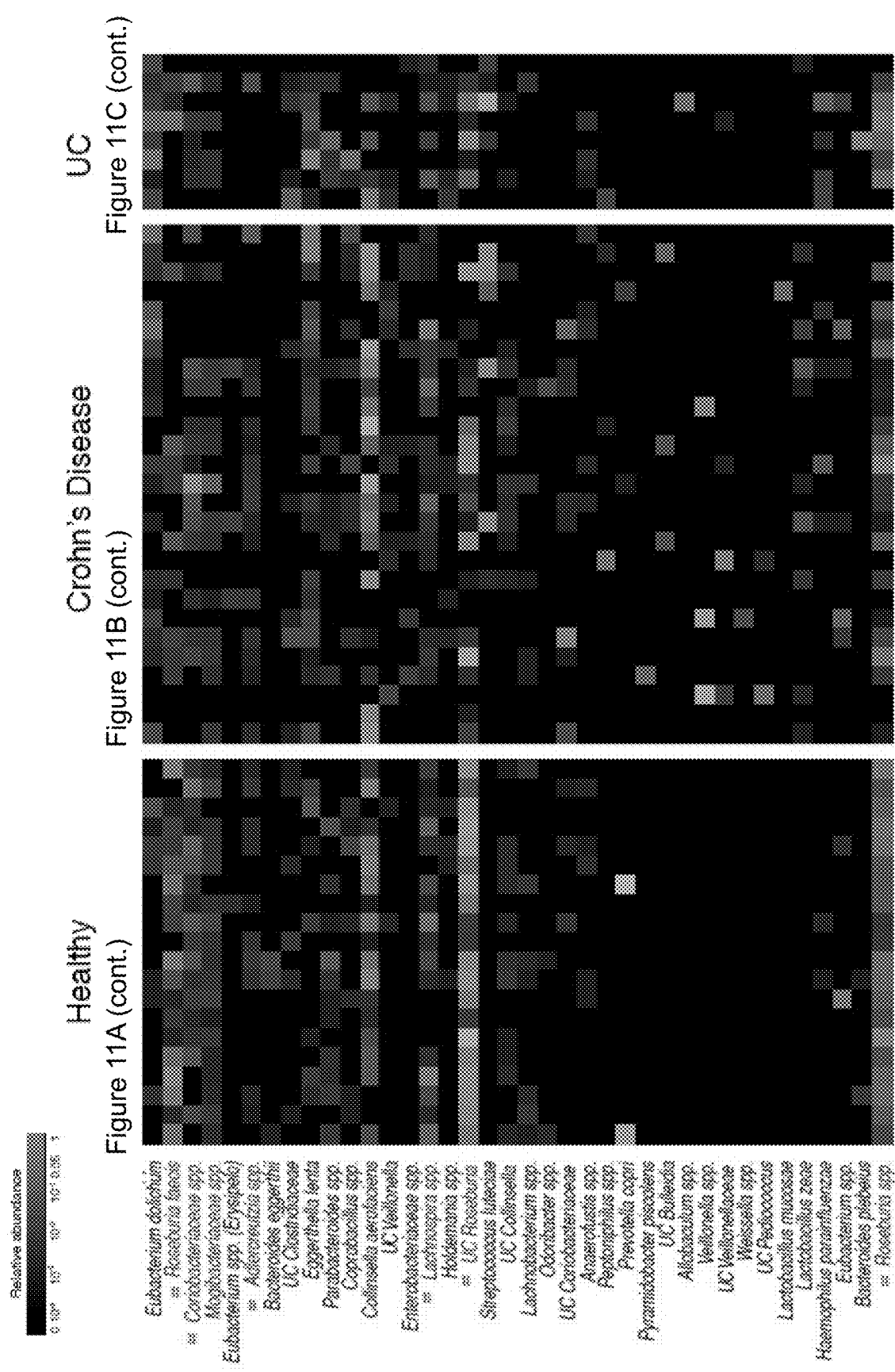

The IgA coating landscape of intestinal bacteria in 20 healthy humans was examined next. As expected, fecal bacteria from human subjects showed variable levels of IgA coating, as measured by flow cytometry (FIG. 10A) (van der Waaij et al., 1996, Gut 38:348; van der Waaij et al., 1994, Cytometry 16:270), and the taxonomic composition of the microbiota varied greatly between subjects (FIG. 11). IgA coating patterns, as measured by ICI, also differed substantially between humans—some subjects showed ICI scores greater than ten for only one or two bacterial species, while others showed high ICI scores for six or more species (FIG. 12). Despite the observed variability in taxonomic composition and IgA coating, clustering analysis (complete linkage clustering using Euclidean distance) of ICI scores of all bacterial taxa revealed a clear pattern of IgA coating across healthy humans, demonstrating that IgA coating of specific bacterial taxa is conserved within the healthy population (FIG. 3A). Statistical comparisons of IgA coated and non-coated fractions revealed six significantly IgA coated bacterial species ($P<0.05$, LEfSe and Wilcoxon rank-sum) (FIG. 13A): an unclassified *Bifidobacterium, Akkermansia muciniphila, Ruminococcus torques, Dorea* spp., an unclassified Erysipelotricaceae, and *Actinomyces* spp. These taxa thus represent the most prevalent and conserved IgA coated bacteria in healthy humans. As in mice, highly coated members of the microbiota may preferentially affect host health and disease through their interactions with the immune system. Interestingly, while the effects of most of the species that were identified as IgA coated are not well characterized in the literature, *Akkermansia muciniphila* was recently found to induce mucus production and lead to weight loss in obese mice (Everard et al., 2013, Proceedings of the National Academy of Sciences of the United States of America 110:9066) and *Bifidobacterium* spp. were found to induce IL-10 producing T regulatory type 1 cells in the colon (Jeon et al., 2012, PLoS pathogens 8:e1002714).

In addition to the conserved IgA coated taxa, multiple taxa were highly coated with IgA in one or more healthy subjects (FIG. 3A). In some cases, these taxa were present in only a single human subject (e.g., Prevotellaceae spp.). In other cases, a taxon was broadly prevalent, but was only coated in a single human subject (e.g., *Coprococcus catus*), consistent with the explanation that genetic, environmental, or unique bacterial factors might determine whether or not these particular taxa are coated with IgA.

While it is known that interactions between the microbiota and the immune system play a critical role in inflammatory bowel diseases (IBD), such as Crohn's Disease (CD) and Ulcerative Colitis (UC) (Strober, 2013, Trends in immunology 34:423), the identities of specific immunomodulatory bacteria in these diseases are not known. Therefore, IgA coating in fecal samples from 27 patients with Crohn's disease and 8 patients with Ulcerative Colitis was examined (FIGS. 3B and 3C, and FIG. 10). As was observed in healthy controls, IBD patients exhibited significant variability in their microbiota compositions (FIGS. 11B and 11C). Since IBD patients exhibit chronic intestinal inflammation that can lead to disruption of the epithelial barrier, it was expected that IgA coating of all taxa might be increased leading to homogenous coating of the microbiota in IBD. However, like healthy controls, individual IBD patients showed high coating of only a limited number of taxa. When compared with the pattern of IgA coating in control subjects, CD and UC patients showed markedly increased diversity in the bacterial taxa that were highly coated with IgA (FIGS. 3B and 3C). Specific bacterial taxa that were always present but rarely or never coated in control patients were highly coated in one or more IBD patients (e.g., *Faecalibacterium prausnitzii* and *Coprococcus* spp.), which, while not wishing to be bound by any particular theory, is consistent with the explanation that IBD patients mount immune responses to bacteria that are normally ignored. In addition, IBD patients often showed reduced coating of taxa that were consistently coated in control subjects, even when the relative abundance of that taxon was not significantly altered; for example, average coating of *Dorea* spp. was reduced overall when comparing ICIs of control and CD patients ($P<0.05$, LEfSe and Wilcoxon rank-sum). Overall, IBD patients as a group showed a dramatically altered pattern of IgA coating as compared to controls: four of the six taxa that were consistently coated in controls were not significantly coated in IBD patients, and UC patients 'exchanged' their IgA coated unclassified *Bifidobacterium* for a different *Bifidobacterium* spp. Furthermore, both CD and UC patients showed high coating of members of the *Streptococcus* genus, which were not coated with IgA in healthy controls ($P<0.05$, LEfSe and Wilcoxon rank-sum).

Multiple taxa that were uniquely present in IBD were highly coated in at least one patient (e.g., unclassified *Bulleidia, Allobaculum* spp., *Lactobacillus mucosae*, unclassified *Pediococcus*, and *Weissella* spp.). In addition, multiple species that were rarely present and never highly coated in control subjects were highly coated in multiple IBD patients (e.g., *Streptococcus luteciae, Haemophilus parainfluenzae*, and *Lactobacillus zeae*)(See Table 1). Because transmissible members of the $Asc^{-/-}$ mouse microbiota become highly IgA coated in wild type recipient animals, and these recipients exhibit increased sensitivity to colitis, IBD-specific IgA coated bacteria present interesting candidates for bacteria that may drive inflammation in IBD.

TABLE 1

| | Frequency of Subjects with ICI > 10 | | |
| --- | --- | --- | --- |
| | Control | CD | UC |
| Highly Coated in UC and CD but not Control | | | |
| *Streptococcus luteciae* | 0.0 | 14.8 | 12.5 |
| *Coprococcus* | 0.0 | 14.8 | 12.5 |
| *Haemophilus parainfluenzae* | 0.0 | 11.1 | 37.5 |
| *Faecalibacterium prausnitzii* | 0.0 | 7.4 | 25.0 |
| *Collinsella aerofaciens* | 0.0 | 7.4 | 12.5 |
| *Blautia obeum* | 0.0 | 7.4 | 12.5 |
| *Oscillospira* | 0.0 | 3.7 | 25.0 |
| *Turicibacter* | 0.0 | 3.7 | 12.5 |
| *Clostridium perfringens* | 0.0 | 3.7 | 12.5 |
| *Veillonella dispar* | 0.0 | 3.7 | 12.5 |
| Highly Coated in CD but not Control or UC | | | |
| *Blautia* | 0.0 | 14.8 | 0.0 |
| *Lactobacillus* Other | 0.0 | 11.1 | 0.0 |

TABLE 1-continued

|  | Frequency of Subjects with ICI > 10 | | |
| --- | --- | --- | --- |
|  | Control | CD | UC |
| *Clostridium* | 0.0 | 11.1 | 0.0 |
| UC Ruminococcaceae | 0.0 | 11.1 | 0.0 |
| *Lactobacillus* | 0.0 | 7.4 | 0.0 |
| *Lactobacillus reuteri* | 0.0 | 7.4 | 0.0 |
| *Pediococcus* Other | 0.0 | 7.4 | 0.0 |
| *Acidaminococcus* | 0.0 | 7.4 | 0.0 |
| *Bacteroides* Other | 0.0 | 3.7 | 0.0 |
| *Bacteroides* | 0.0 | 3.7 | 0.0 |
| *Lactobacillus mucosae* | 0.0 | 3.7 | 0.0 |
| *Weissella* | 0.0 | 3.7 | 0.0 |
| UC Clostridiales | 0.0 | 3.7 | 0.0 |
| *Anaerostipes* | 0.0 | 3.7 | 0.0 |
| *Roseburia* | 0.0 | 3.7 | 0.0 |
| *Roseburia faecis* | 0.0 | 3.7 | 0.0 |
| *Veillonella* | 0.0 | 3.7 | 0.0 |
| *Bulleidia* Other | 0.0 | 3.7 | 0.0 |
| [*Eubacterium*] | 0.0 | 3.7 | 0.0 |
| Highly Coated in UC but not Control or CD | | | |
| *Rikenellaceae* | 0.0 | 0.0 | 25.0 |
| *Lactobacillus zeae* | 0.0 | 0.0 | 25.0 |
| [*Eubacterium*] *dolichum* | 0.0 | 0.0 | 25.0 |
| *Eggerthella lenta* | 0.0 | 0.0 | 12.5 |
| *Ruminococcus* | 0.0 | 0.0 | 12.5 |
| *Allobaculum* | 0.0 | 0.0 | 12.5 |
| More frequently coated in UC or CD than Control | | | |
| UC Erysipelotrichaceae | 20.0 | 25.9 | 37.5 |
| *Actinomyces* | 5.0 | 22.2 | 25.0 |
| *Streptococcus* | 5.0 | 18.5 | 25.0 |
| *Dialister* | 5.0 | 18.5 | 25.0 |
| *Blautia producta* | 5.0 | 18.5 | 12.5 |
| Erysipelotrichaceae | 10.0 | 14.8 | 50.0 |
| *Bifidobacterium* | 20.0 | 14.8 | 37.5 |
| [*Ruminococcus*] *gnavus* | 15.0 | 14.8 | 25.0 |
| *Bifidobacterium* Other | 25.0 | 11.1 | 50.0 |
| *Blautia* Other | 5.0 | 11.1 | 25.0 |
| *Streptococcus* Other | 10.0 | 11.1 | 0.0 |
| SMB53 | 10.0 | 11.1 | 0.0 |
| *Coprococcus catus* | 5.0 | 7.4 | 0.0 |
| Ruminococcaceae | 5.0 | 7.4 | 0.0 |
| [*Eubacterium*] *biforme* | 5.0 | 7.4 | 0.0 |
| *Ruminococcus bromii* | 20.0 | 3.7 | 25.0 |
| *Bifidobacterium adolescentis* | 5.0 | 3.7 | 12.5 |
| Lachnospiraceae_other | 10.0 | 3.7 | 12.5 |
| *Bacteroides fragilis* | 5.0 | 0.0 | 50.0 |
| Lachnospiraceae | 5.0 | 0.0 | 12.5 |
| *Sutterella* | 5.0 | 0.0 | 12.5 |
| More frequently coated in Control than UC or CD | | | |
| *Akkermansia muciniphila* | 55.0 | 7.4 | 25.0 |
| [*Ruminococcus*] *torques* | 50.0 | 25.9 | 25.0 |
| *Dorea* | 40.0 | 18.5 | 0.0 |
| *Dorea formicigenerans* | 30.0 | 11.1 | 0.0 |
| UC Enterobacteriaceae | 30.0 | 22.2 | 12.5 |
| UC *Faecalibacterium* | 20.0 | 7.4 | 0.0 |
| UC *Dorea* | 15.0 | 0.0 | 0.0 |
| *Ruminococcus callidus* | 10.0 | 0.0 | 0.0 |
| *Methanobrevibacter* | 10.0 | 3.7 | 0.0 |
| Clostridiales | 10.0 | 3.7 | 0.0 |
| UC [*Ruminococcus*] | 10.0 | 7.4 | 0.0 |
| [*Ruminococcus*] | 10.0 | 7.4 | 0.0 |
| *Parabacteroides distasonis* | 5.0 | 0.0 | 0.0 |
| *Paraprevotella* | 5.0 | 0.0 | 0.0 |
| [*Prevotella*] | 5.0 | 0.0 | 0.0 |
| *Lactococcus* | 5.0 | 0.0 | 0.0 |
| Christensenellaceae | 5.0 | 0.0 | 0.0 |
| *Coprococcus* Other | 5.0 | 0.0 | 0.0 |
| *Coprococcus eutactus* | 5.0 | 0.0 | 0.0 |
| *Ruminococcus* Other | 5.0 | 0.0 | 0.0 |
| *Bilophila* | 5.0 | 0.0 | 0.0 |
| *Slackia* | 5.0 | 3.7 | 0.0 |
| UC *Parabacteroides* | 5.0 | 3.7 | 0.0 |
| *Megasphaera* | 5.0 | 3.7 | 0.0 |

Many factors can potentially influence IgA coating of specific members of the microbiota, including bacterial abundance, location, the immunogenicity of particular bacterial epitopes, and bacterial evasion mechanisms, such as epitope masking or antigenic drift (Macpherson 2012, Immunological reviews 245:132). Furthermore, host genetics and the composition of the remaining members of the microbiota may also affect patterns of IgA coating. Despite this apparent complexity, it was found that a limited number of taxa were highly coated with IgA in mice and humans in both health and disease. These taxa thus preferentially stimulate intestinal immune responses, possibly because they penetrate the mucus barrier and interact directly with cells of the mucosal immune system. Indeed, many of the highly coated taxa identified in mice are known to have broad effects on the immune system and, therefore, on disease susceptibility. Importantly, the immunomodulatory effects of almost all of the highly coated bacteria that were identified in humans remain unexplored. Integrating 16S-based microbiota profiling with taxa-specific information regarding the host immune response may enhance predictions of disease susceptibility and enable personalized approaches to disease prevention and treatment.

Experiments were conducted to evaluate and compare the IgA coating of fecal bacteria in healthy and obese adolescents. Depicted in the main heatmap are IgA coating index (ICI) scores for bacterial species from 4 healthy and 15 obese adolescents (FIG. 14). Each column represents an individual human subject. Bacterial taxa are clustered (complete linkage clustering using Euclidean distance) based ICI scores. Bacterial taxa from obese patients with significantly higher relative abundance in the IgA+ fraction as compared to the IgA− fraction by LEfSe are considered to be highly coated with IgA and are labeled in red (###) (FIG. 14).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating non-alcoholic steatohepatitis (NASH) in a subject in need thereof, the method comprising administering to the subject at least one therapy, wherein the at least one therapy induces an immune response directed against a secretory antibody-bound bacteria in the microbiota of the subject that contributes to the development or progression of NASH.

2. The method of claim 1, wherein the at least one therapy is selected from the group consisting of at least one vaccine and at least one passive immunotherapy.

3. The method of claim 1, wherein the at least one therapy comprises at least one vaccine.

4. The method of claim 1, wherein the secretory antibody-bound bacteria is at least one of Segmented Filamentous Bacteria (SFB), *Lactobacillus, Helicobacter*, S24-7, Erysipelotrichaceae, Prevotellaceae, *Eubacterium, Acidaminococcus, Actinomyces, Allobaculum, Anaerostipes, Bacteroides, Bifidobacterium, Blautia, Clostridium, Coprococcus, Dialister*, Erysipelotrichaceae, Lachnospiraceae, *Lactobacillus, Oscillospira*, Rikenellaceae, *Roseburia*, Ruminococcaceae, *Ruminococcus*, SMB53, *Streptococcus, Sutterella, Turicibacter*, UC Clostridiales, UC Erysipelotrichaceae, UC Ruminococcaceae, *Veillonella* and *Weissella*.

5. The method of claim 1, wherein the secretory antibody-bound bacteria is at least one of *Heliobacter flexispira, Eubacterium biforme, Eubacterium dolichum, Ruminococcus gnavus, Bacteroides fragilis, Bifidobacterium adolescentis, Blautia obeum, Blautia producta, Clostridium perfringens, Collinsella aerofaciens, Coprococcus catus, Eggerthella lenta, Faecalibacterium prausnitzii, Haemophilus parainfluenzae, Lactobacillus mucosae, Lactobacillus reuteri, Lactobacillus zeae, Roseburia faecis*, Ruminococcaceae, *Ruminococcus, Ruminococcus bromii, Streptococcus luteciae* and *Veillonella dispar.*

6. The method of claim 1, further comprising diagnosing NASH in the subject prior to administering the at least one therapy, wherein the diagnosing comprises the steps of:
   (a) isolating secretory an antibody-bound bacteria from a biological sample obtained from the subject;
   (b) amplifying bacterial nucleic acid from the secretory antibody bound bacteria so isolated;
   (c) determining sequences of the bacterial nucleic acid so amplified; and
   (d) identifying the type of antibody-bound bacteria present in the biological sample by identifying nucleic acid sequences that are indicative of particular types of bacteria, wherein when the type of antibody-bound bacteria present in the subject's biological sample is a type of bacteria that contributes to the development or progression of NASH, the subject is diagnosed with NASH.

7. The method of claim 6, wherein the biological sample is at least one of a fecal sample, a mucus sample, a sputum sample, and a breast milk sample.

8. The method of claim 6, wherein the bacterial nucleic acid is a gene encoding 16S rRNA.

9. The method of claim 6, wherein the isolating is step (a) comprises:
   (i) performing a first round of cell sorting; and
   (ii) performing a second round of cell sorting on a secretory antibody-positive fraction obtained from the first round of cell sorting.

10. The method of claim 9, wherein the first round of cell sorting is performed using magnetic activated cell sorting.

11. The method of claim 10, wherein the second round of cell sorting is performed using fluorescence activated cell sorting.

12. A method of treating inflammatory bowel disease (IBD) in a subject in need thereof, the method comprising administering to the subject at least one therapy, wherein the at least one therapy induces an immune response directed against a secretory antibody-bound bacteria in the microbiota of the subject that contributes to the development or progression of IBD.

13. The method of claim 12, wherein the at least one therapy is selected from the group consisting of at least one vaccine and at least one passive immunotherapy.

14. The method of claim 12, wherein the at least one therapy comprises at least one vaccine.

15. The method of claim 12, wherein the secretory antibody-bound bacteria is at least one of Segmented Filamentous Bacteria (SFB), *Lactobacillus, Helicobacter*, S24-7, Erysipelotrichaceae, Prevotellaceae, *Eubacterium, Acidaminococcus, Actinomyces, Allobaculum, Anaerostipes, Bacteroides, Bifidobacterium, Blautia, Clostridium, Coprococcus, Dialister,* Erysipelotrichaceae, Lachnospiraceae, *Lactobacillus, Oscillospira,* Rikenellaceae, *Roseburia,* Ruminococcaceae, *Ruminococcus,* SMB53, *Streptococcus, Sutterella, Turicibacter,* UC Clostridiales, UC Erysipelotrichaceae, UC Ruminococcaceae, *Veillonella* and *Weissella.*

16. The method of claim 12, wherein the secretory antibody-bound bacteria is at least one of *Heliobacier flexispira, Eubacierium biforme, Eubacterium dolichum, Ruminococcus gnavus, Bacteroides fragilis, Bifidobacterium adolescentis, Blautia obeum, Blautia producta, Clostridium perfringens, Collinsella aerofaciens, Coprococcus caus, Eggerthella lenta, Faecalibacterium prausnitzii, Haemophilus parainfluenzae, Lactobacillus mucosae, Lactobacillus reuteri, Lactobacillus zeae, Roseburia faecis*, Ruminococcaceae, *Ruminococcus, Ruminococcus bromii, Streptococcus luteciae* and *Veillonella dispar.*

17. The method of claim 12, further comprising diagnosing IBD in the subject prior to administering the at least one therapy, wherein the diagnosing comprises the steps of:
   (a) isolating secretory an antibody-bound bacteria from a biological sample obtained from the subject;
   (b) amplifying bacterial nucleic acid from the secretory antibody bound bacteria so isolated;
   (c) determining sequences of the bacterial nucleic acid so amplified; and
   (d) identifying the type of antibody-bound bacteria present in the biological sample by identifying nucleic acid sequences that are indicative of particular types of bacteria, wherein when the type of antibody-bound bacteria present in the subject's biological sample is a type of bacteria that contributes to the development or progression of IBD, the subject is diagnosed with IBD.

18. The method of claim 17, wherein the biological sample is at least one of a fecal sample, a mucus sample, a sputum sample, and a breast milk sample.

19. The method of claim 17, wherein the bacterial nucleic acid is a gene encoding 16S rRNA.

20. The method of claim 17, wherein the isolating is step (a) comprises:
   (i) performing a first round of cell sorting; and
   (ii) performing a second round of cell sorting on a secretory antibody-positive fraction obtained from the first round of cell sorting.

21. The method of claim 20, wherein the first round of cell sorting is performed using magnetic activated cell sorting.

22. The method of claim 21, wherein the second round of cell sorting is performed using fluorescence activated cell sorting.

* * * * *